United States Patent
Pachner et al.

(10) Patent No.: US 10,309,287 B2
(45) Date of Patent: Jun. 4, 2019

(54) INFERENTIAL SENSOR

(71) Applicant: Garrett Transportation I Inc., Torrance, CA (US)

(72) Inventors: Daniel Pachner, Prague (CZ); Michael Uchanski, Vevey (CH); Lucas Lansky, Prague (CZ)

(73) Assignee: GARRETT TRANSPORTATION I INC., Torrance, CA (US)

( * ) Notice: Subject to any disclaimer, the term of this patent is extended or adjusted under 35 U.S.C. 154(b) by 0 days.

(21) Appl. No.: 15/782,669

(22) Filed: Oct. 12, 2017

(65) Prior Publication Data
US 2018/0149064 A1    May 31, 2018

Related U.S. Application Data

(63) Continuation-in-part of application No. PCT/US2016/064036, filed on Nov. 29, 2016.

(51) Int. Cl.
*F01N 11/00*    (2006.01)
*F01N 9/00*    (2006.01)
(Continued)

(52) U.S. Cl.
CPC ............ *F01N 11/005* (2013.01); *F01N 3/208* (2013.01); *F01N 9/005* (2013.01); *F01N 11/007* (2013.01); *F02D 41/0072* (2013.01); *F02D 41/1458* (2013.01); *F02M 35/1038* (2013.01); *G01N 33/0037* (2013.01); *F01N 2560/026* (2013.01); *F01N 2900/14* (2013.01); *F02D 41/1456* (2013.01); *F02D 41/2451* (2013.01); *F02D 41/2454* (2013.01); *F02D 2200/0402* (2013.01); *F02D 2200/0406* (2013.01); *F02D 2200/0411* (2013.01); *F02D 2200/0414* (2013.01);
(Continued)

(58) Field of Classification Search
CPC ............... F01N 11/005; F01N 11/0065; F01N 11/0077; F01N 9/0005; F02D 41/0072; F02D 41/1458
USPC ..................................... 123/568.21
See application file for complete search history.

(56) References Cited

U.S. PATENT DOCUMENTS

| 3,744,461 A | 7/1973 | Davis |
| 4,005,578 A | 2/1977 | McInerney |

(Continued)

FOREIGN PATENT DOCUMENTS

| CN | 102063561 A | 5/2011 |
| CN | 102331350 A | 1/2012 |

(Continued)

OTHER PUBLICATIONS

"Aftertreatment Modeling of RCCI Engine During Transient Operation," University of Wisconsin—Engine Research Center, 1 page, May 31, 2014.

(Continued)

*Primary Examiner* — Mahmoud Gimie
(74) *Attorney, Agent, or Firm* — Seager, Tufte & Wickhem, LLP

(57) ABSTRACT

A system and an approach for determining various pressures or flows in an internal combustion engine, such as a pressure adjacent a recirculation exhaust gas flow through a controlled valve of an engine. Also, among the sensors accommodated in the system, is a pressure sensor sensing a pressure in an intake manifold of the engine.

18 Claims, 3 Drawing Sheets

(51) Int. Cl.

| | | |
|---|---|---|
| F01N 3/20 | (2006.01) | |
| F02M 35/10 | (2006.01) | |
| G01N 33/00 | (2006.01) | |
| F02D 41/00 | (2006.01) | |
| F02D 41/14 | (2006.01) | |
| F02D 41/24 | (2006.01) | |

(52) U.S. Cl.
CPC ..... *F02D 2200/0418* (2013.01); *Y02A 50/245* (2018.01); *Y02T 10/47* (2013.01)

(56) References Cited

U.S. PATENT DOCUMENTS

| | | |
|---|---|---|
| 4,055,158 A | 10/1977 | Marsee |
| 4,206,606 A | 6/1980 | Yamada |
| 4,252,098 A | 2/1981 | Tomczak et al. |
| 4,359,991 A | 11/1982 | Stumpp et al. |
| 4,383,441 A | 5/1983 | Willis et al. |
| 4,426,982 A | 1/1984 | Lehner et al. |
| 4,438,497 A | 3/1984 | Willis et al. |
| 4,440,140 A | 4/1984 | Kawagoe et al. |
| 4,456,883 A | 6/1984 | Bullis et al. |
| 4,485,794 A | 12/1984 | Kimberley et al. |
| 4,601,270 A | 7/1986 | Kimberley et al. |
| 4,616,308 A | 10/1986 | Morshedi et al. |
| 4,653,449 A | 3/1987 | Kamel et al. |
| 4,671,235 A | 6/1987 | Hosaka |
| 4,735,181 A | 4/1988 | Kaneko et al. |
| 4,947,334 A | 8/1990 | Massey et al. |
| 4,962,570 A | 10/1990 | Hosaka et al. |
| 5,044,337 A | 9/1991 | Williams |
| 5,076,237 A | 12/1991 | Hartman et al. |
| 5,089,236 A | 2/1992 | Clerc |
| 5,094,213 A | 3/1992 | Dudek et al. |
| 5,095,874 A | 3/1992 | Schnaibel et al. |
| 5,108,716 A | 4/1992 | Nishizawa et al. |
| 5,123,397 A | 6/1992 | Richeson |
| 5,150,289 A | 9/1992 | Badavas |
| 5,186,081 A | 2/1993 | Richardson et al. |
| 5,233,829 A | 8/1993 | Komatsu |
| 5,270,935 A | 12/1993 | Dudek et al. |
| 5,273,019 A | 12/1993 | Matthews et al. |
| 5,282,449 A | 2/1994 | Takahashi et al. |
| 5,293,553 A | 3/1994 | Dudek et al. |
| 5,349,816 A | 9/1994 | Sanbayashi et al. |
| 5,365,734 A | 11/1994 | Takeshima |
| 5,394,322 A | 2/1995 | Hansen |
| 5,394,331 A | 2/1995 | Dudek et al. |
| 5,398,502 A | 3/1995 | Watanabe |
| 5,408,406 A | 4/1995 | Mathur et al. |
| 5,431,139 A | 7/1995 | Grutter et al. |
| 5,452,576 A | 9/1995 | Hamburg et al. |
| 5,477,840 A | 12/1995 | Neumann |
| 5,560,208 A | 10/1996 | Halimi et al. |
| 5,570,574 A | 11/1996 | Yamashita et al. |
| 5,598,825 A | 2/1997 | Neumann |
| 5,609,139 A | 3/1997 | Ueda et al. |
| 5,611,198 A | 3/1997 | Lane et al. |
| 5,682,317 A | 10/1997 | Keeler et al. |
| 5,690,086 A | 11/1997 | Kawano et al. |
| 5,692,478 A | 12/1997 | Nogi et al. |
| 5,697,339 A | 12/1997 | Esposito |
| 5,704,011 A | 12/1997 | Hansen et al. |
| 5,740,033 A | 4/1998 | Wassick et al. |
| 5,746,183 A | 5/1998 | Parke et al. |
| 5,765,533 A | 6/1998 | Nakajima |
| 5,771,867 A | 6/1998 | Amstutz et al. |
| 5,785,030 A | 7/1998 | Paas |
| 5,788,004 A | 8/1998 | Friedmann et al. |
| 5,842,340 A | 12/1998 | Bush et al. |
| 5,846,157 A | 12/1998 | Reinke et al. |
| 5,893,092 A | 4/1999 | Driscoll |
| 5,917,405 A | 6/1999 | Joao |
| 5,924,280 A | 7/1999 | Tarabulski |
| 5,942,195 A | 8/1999 | Lecea et al. |
| 5,964,199 A | 10/1999 | Atago et al. |
| 5,970,075 A | 10/1999 | Wasada |
| 5,974,788 A | 11/1999 | Hepburn et al. |
| 5,995,895 A | 11/1999 | Watt et al. |
| 6,029,626 A | 2/2000 | Bruestle |
| 6,035,640 A | 3/2000 | Kolmanovsky et al. |
| 6,048,620 A | 4/2000 | Zhong et al. |
| 6,048,628 A | 4/2000 | Hilman et al. |
| 6,055,810 A | 5/2000 | Borland et al. |
| 6,056,781 A | 5/2000 | Wassick et al. |
| 6,058,700 A | 5/2000 | Yamashita et al. |
| 6,067,800 A | 5/2000 | Kolmanovsky et al. |
| 6,076,353 A | 6/2000 | Freudenberg et al. |
| 6,105,365 A | 8/2000 | Deeba et al. |
| 6,122,555 A | 9/2000 | Lu |
| 6,134,883 A | 10/2000 | Kato et al. |
| 6,153,159 A | 11/2000 | Engeler et al. |
| 6,161,528 A | 12/2000 | Akao et al. |
| 6,170,259 B1 | 1/2001 | Boegner et al. |
| 6,171,556 B1 | 1/2001 | Burk et al. |
| 6,178,743 B1 | 1/2001 | Hirota et al. |
| 6,178,749 B1 | 1/2001 | Kolmanovsky et al. |
| 6,208,914 B1 | 3/2001 | Ward et al. |
| 6,216,083 B1 | 4/2001 | Ulyanov et al. |
| 6,233,922 B1 | 5/2001 | Maloney |
| 6,236,956 B1 | 5/2001 | Mantooth et al. |
| 6,237,330 B1 | 5/2001 | Takahashi et al. |
| 6,242,873 B1 | 6/2001 | Drozdz et al. |
| 6,263,672 B1 | 7/2001 | Roby et al. |
| 6,273,060 B1 | 8/2001 | Cullen |
| 6,279,551 B1 | 8/2001 | Iwano et al. |
| 6,312,538 B1 | 11/2001 | Latypov et al. |
| 6,314,351 B1 | 11/2001 | Chutorash |
| 6,314,662 B1 | 11/2001 | Ellis, III |
| 6,314,724 B1 | 11/2001 | Kakuyama et al. |
| 6,321,538 B2 | 11/2001 | Hasler et al. |
| 6,327,361 B1 | 12/2001 | Harshavardhana et al. |
| 6,338,245 B1 | 1/2002 | Shimoda et al. |
| 6,341,487 B1 | 1/2002 | Takahashi et al. |
| 6,347,619 B1 | 2/2002 | Whiting et al. |
| 6,360,159 B1 | 3/2002 | Miller et al. |
| 6,360,541 B2 | 3/2002 | Waszkiewicz et al. |
| 6,360,732 B1 | 3/2002 | Bailey et al. |
| 6,363,715 B1 | 4/2002 | Bidner et al. |
| 6,363,907 B1 | 4/2002 | Arai et al. |
| 6,379,281 B1 | 4/2002 | Collins et al. |
| 6,389,203 B1 | 5/2002 | Jordan et al. |
| 6,425,371 B2 | 7/2002 | Majima |
| 6,427,436 B1 | 8/2002 | Allansson et al. |
| 6,431,160 B1 | 8/2002 | Sugiyama et al. |
| 6,445,963 B1 | 9/2002 | Blevins et al. |
| 6,446,430 B1 | 9/2002 | Roth et al. |
| 6,453,308 B1 | 9/2002 | Zhao et al. |
| 6,463,733 B1 | 9/2002 | Zhao et al. |
| 6,463,734 B1 | 10/2002 | Tamura et al. |
| 6,466,893 B1 | 10/2002 | Latwesen et al. |
| 6,470,682 B2 | 10/2002 | Gray, Jr. |
| 6,470,862 B2 | 10/2002 | Isobe et al. |
| 6,470,886 B1 | 10/2002 | Jestrabek-Hart |
| 6,481,139 B2 | 11/2002 | Weldle |
| 6,494,038 B2 | 12/2002 | Kobayashi et al. |
| 6,502,391 B1 | 1/2003 | Hirota et al. |
| 6,505,465 B2 | 1/2003 | Kanazawa et al. |
| 6,510,351 B1 | 1/2003 | Blevins et al. |
| 6,512,974 B2 | 1/2003 | Houston et al. |
| 6,513,495 B1 | 2/2003 | Franke et al. |
| 6,532,433 B2 | 3/2003 | Bharadwaj et al. |
| 6,542,076 B1 | 4/2003 | Joao |
| 6,546,329 B2 | 4/2003 | Bellinger |
| 6,549,130 B1 | 4/2003 | Joao |
| 6,550,307 B1 | 4/2003 | Zhang et al. |
| 6,553,754 B2 | 4/2003 | Meyer et al. |
| 6,560,528 B1 | 5/2003 | Gitlin et al. |
| 6,560,960 B2 | 5/2003 | Nishimura et al. |
| 6,571,191 B1 | 5/2003 | York et al. |
| 6,579,206 B2 | 6/2003 | Liu et al. |
| 6,591,605 B2 | 7/2003 | Lewis |
| 6,594,990 B2 | 7/2003 | Kuenstler et al. |
| 6,601,387 B2 | 8/2003 | Zurawski et al. |

(56) References Cited

U.S. PATENT DOCUMENTS

| | | |
|---|---|---|
| 6,612,293 B2 | 9/2003 | Schweinzer et al. |
| 6,615,584 B2 | 9/2003 | Ostertag |
| 6,625,978 B1 | 9/2003 | Eriksson et al. |
| 6,629,408 B1 | 10/2003 | Murakami et al. |
| 6,637,382 B1 | 10/2003 | Brehob et al. |
| 6,644,017 B2 | 11/2003 | Takahashi et al. |
| 6,647,710 B2 | 11/2003 | Nishiyama et al. |
| 6,647,971 B2 | 11/2003 | Vaughan et al. |
| 6,651,614 B2 | 11/2003 | Flamig-Vetter et al. |
| 6,662,058 B1 | 12/2003 | Sanchez |
| 6,666,198 B2 | 12/2003 | Mitsutani |
| 6,666,410 B2 | 12/2003 | Boelitz et al. |
| 6,671,596 B2 | 12/2003 | Kawashima et al. |
| 6,671,603 B2 | 12/2003 | Cari et al. |
| 6,672,052 B2 | 1/2004 | Taga et al. |
| 6,672,060 B1 | 1/2004 | Buckland et al. |
| 6,679,050 B1 | 1/2004 | Takahashi et al. |
| 6,687,597 B2 | 2/2004 | Sulatisky et al. |
| 6,688,283 B2 | 2/2004 | Jaye |
| 6,694,244 B2 | 2/2004 | Meyer et al. |
| 6,694,724 B2 | 2/2004 | Tanaka et al. |
| 6,705,084 B2 | 3/2004 | Allen et al. |
| 6,718,254 B2 | 4/2004 | Hashimoto et al. |
| 6,718,753 B2 | 4/2004 | Bromberg et al. |
| 6,725,208 B1 | 4/2004 | Hartman et al. |
| 6,732,522 B2 * | 5/2004 | Wright .............. F02D 41/145 123/559.1 |
| 6,736,120 B2 | 5/2004 | Sumilla |
| 6,738,682 B1 | 5/2004 | Pasadyn |
| 6,739,122 B2 | 5/2004 | Kitajima et al. |
| 6,742,330 B2 | 6/2004 | Genderen |
| 6,743,352 B2 | 6/2004 | Ando et al. |
| 6,748,936 B2 | 6/2004 | Kinomura et al. |
| 6,752,131 B2 | 6/2004 | Poola et al. |
| 6,752,135 B2 | 6/2004 | McLaughlin et al. |
| 6,757,579 B1 | 6/2004 | Pasadyn |
| 6,758,037 B2 | 7/2004 | Terada et al. |
| 6,760,631 B1 | 7/2004 | Berkowitz et al. |
| 6,760,657 B2 | 7/2004 | Katoh |
| 6,760,658 B2 | 7/2004 | Yasui et al. |
| 6,770,009 B2 | 8/2004 | Badillo et al. |
| 6,772,585 B2 | 8/2004 | Iihoshi et al. |
| 6,775,623 B2 | 8/2004 | Ali et al. |
| 6,779,344 B2 | 8/2004 | Hartman et al. |
| 6,779,512 B2 | 8/2004 | Mitsutani |
| 6,788,072 B2 | 9/2004 | Nagy et al. |
| 6,789,533 B1 | 9/2004 | Hashimoto et al. |
| 6,792,927 B2 | 9/2004 | Kobayashi |
| 6,804,618 B2 | 10/2004 | Junk |
| 6,814,062 B2 | 11/2004 | Esteghlal et al. |
| 6,817,171 B2 | 11/2004 | Zhu |
| 6,823,667 B2 | 11/2004 | Braun et al. |
| 6,826,903 B2 | 12/2004 | Yahata et al. |
| 6,827,060 B2 | 12/2004 | Huh |
| 6,827,061 B2 | 12/2004 | Nytomt et al. |
| 6,827,070 B2 | 12/2004 | Fehl et al. |
| 6,834,497 B2 | 12/2004 | Miyoshi et al. |
| 6,837,042 B2 | 1/2005 | Colignon et al. |
| 6,839,637 B2 | 1/2005 | Moteki et al. |
| 6,849,030 B2 | 2/2005 | Yamamoto et al. |
| 6,857,264 B2 | 2/2005 | Ament |
| 6,873,675 B2 | 3/2005 | Kurady et al. |
| 6,874,467 B2 | 4/2005 | Hunt et al. |
| 6,879,906 B2 | 4/2005 | Makki et al. |
| 6,882,929 B2 | 4/2005 | Liang et al. |
| 6,904,751 B2 | 6/2005 | Makki et al. |
| 6,911,414 B2 | 6/2005 | Kimura et al. |
| 6,915,779 B2 | 7/2005 | Sriprakash |
| 6,920,865 B2 | 7/2005 | Lyon |
| 6,923,902 B2 | 8/2005 | Ando et al. |
| 6,925,372 B2 | 8/2005 | Yasui |
| 6,925,796 B2 | 8/2005 | Nieuwstadt et al. |
| 6,928,362 B2 | 8/2005 | Meaney |
| 6,928,817 B2 | 8/2005 | Ahmad |
| 6,931,840 B2 | 8/2005 | Strayer et al. |
| 6,934,931 B2 | 8/2005 | Plumer et al. |
| 6,941,744 B2 | 9/2005 | Tanaka |
| 6,945,033 B2 | 9/2005 | Sealy et al. |
| 6,948,310 B2 | 9/2005 | Roberts, Jr. et al. |
| 6,953,024 B2 | 10/2005 | Linna et al. |
| 6,965,826 B2 | 11/2005 | Andres et al. |
| 6,968,677 B2 | 11/2005 | Tamura |
| 6,971,258 B2 | 12/2005 | Rhodes et al. |
| 6,973,382 B2 | 12/2005 | Rodriguez et al. |
| 6,978,744 B2 | 12/2005 | Yuasa et al. |
| 6,988,017 B2 | 1/2006 | Pasadyn et al. |
| 6,990,401 B2 | 1/2006 | Neiss et al. |
| 6,996,975 B2 | 2/2006 | Radhamohan et al. |
| 7,000,379 B2 | 2/2006 | Makki et al. |
| 7,013,637 B2 | 3/2006 | Yoshida |
| 7,016,779 B2 | 3/2006 | Bowyer |
| 7,028,464 B2 | 4/2006 | Rosel et al. |
| 7,039,475 B2 | 5/2006 | Sayyarrodsari et al. |
| 7,047,938 B2 | 5/2006 | Flynn et al. |
| 7,050,863 B2 | 5/2006 | Mehta et al. |
| 7,052,434 B2 | 5/2006 | Makino et al. |
| 7,055,311 B2 | 6/2006 | Beutel et al. |
| 7,059,112 B2 | 6/2006 | Bidner et al. |
| 7,063,080 B2 | 6/2006 | Kita et al. |
| 7,067,319 B2 | 6/2006 | Wills et al. |
| 7,069,903 B2 | 7/2006 | Sumilla et al. |
| 7,082,753 B2 | 8/2006 | Dalla Betta et al. |
| 7,085,615 B2 | 8/2006 | Persson et al. |
| 7,106,866 B2 | 9/2006 | Astorino et al. |
| 7,107,978 B2 | 9/2006 | Itoyama |
| 7,111,450 B2 | 9/2006 | Sumilla |
| 7,111,455 B2 | 9/2006 | Okugawa et al. |
| 7,113,835 B2 | 9/2006 | Boyen et al. |
| 7,117,046 B2 | 10/2006 | Boyden et al. |
| 7,124,013 B2 | 10/2006 | Yasui |
| 7,149,590 B2 | 12/2006 | Martin et al. |
| 7,151,976 B2 | 12/2006 | Lin |
| 7,152,023 B2 | 12/2006 | Das |
| 7,155,334 B1 | 12/2006 | Stewart et al. |
| 7,164,800 B2 | 1/2007 | Sun |
| 7,165,393 B2 | 1/2007 | Betta et al. |
| 7,165,399 B2 | 1/2007 | Stewart |
| 7,168,239 B2 | 1/2007 | Ingram et al. |
| 7,182,075 B2 | 2/2007 | Shahed et al. |
| 7,184,845 B2 | 2/2007 | Sayyarrodsari et al. |
| 7,184,992 B1 | 2/2007 | Polyak et al. |
| 7,188,637 B2 | 3/2007 | Dreyer et al. |
| 7,194,987 B2 | 3/2007 | Mogi |
| 7,197,485 B2 | 3/2007 | Fuller |
| 7,200,988 B2 | 4/2007 | Yamashita |
| 7,204,079 B2 | 4/2007 | Audoin |
| 7,212,908 B2 | 5/2007 | Li et al. |
| 7,275,374 B2 | 10/2007 | Stewart et al. |
| 7,275,415 B2 | 10/2007 | Rhodes et al. |
| 7,277,010 B2 | 10/2007 | Joao |
| 7,281,368 B2 | 10/2007 | Miyake et al. |
| 7,292,926 B2 | 11/2007 | Schmidt et al. |
| 7,302,937 B2 | 12/2007 | Ma et al. |
| 7,321,834 B2 | 1/2008 | Chu et al. |
| 7,323,036 B2 | 1/2008 | Boyden et al. |
| 7,328,577 B2 | 2/2008 | Stewart et al. |
| 7,337,022 B2 | 2/2008 | Wojsznis et al. |
| 7,349,776 B2 | 3/2008 | Spillane et al. |
| 7,383,118 B2 | 3/2008 | Imai et al. |
| 7,357,125 B2 | 4/2008 | Kolavennu |
| 7,375,374 B2 | 5/2008 | Chen et al. |
| 7,376,471 B2 | 5/2008 | Das et al. |
| 7,380,547 B1 | 6/2008 | Ruiz |
| 7,389,773 B2 | 6/2008 | Stewart et al. |
| 7,392,129 B2 | 6/2008 | Hill et al. |
| 7,397,363 B2 | 7/2008 | Joao |
| 7,398,082 B2 | 7/2008 | Schwinke et al. |
| 7,398,149 B2 | 7/2008 | Ueno et al. |
| 7,400,933 B2 | 7/2008 | Rawlings et al. |
| 7,400,967 B2 | 7/2008 | Ueno et al. |
| 7,413,583 B2 | 8/2008 | Langer et al. |
| 7,415,389 B2 | 8/2008 | Stewart et al. |
| 7,418,372 B2 | 8/2008 | Nishira et al. |
| 7,430,854 B2 | 10/2008 | Yasui et al. |

(56) References Cited

U.S. PATENT DOCUMENTS

| | | |
|---|---|---|
| 7,433,743 B2 | 10/2008 | Pistikopoulos et al. |
| 7,444,191 B2 | 10/2008 | Caldwell et al. |
| 7,444,193 B2 | 10/2008 | Cutler |
| 7,447,554 B2 | 11/2008 | Cutler |
| 7,467,614 B2 | 12/2008 | Stewart et al. |
| 7,469,177 B2 | 12/2008 | Samad et al. |
| 7,474,953 B2 | 1/2009 | Hulser et al. |
| 7,493,236 B1 | 2/2009 | Mock et al. |
| 7,505,879 B2 | 3/2009 | Tomoyasu et al. |
| 7,505,882 B2 | 3/2009 | Jenny et al. |
| 7,515,975 B2 | 4/2009 | Stewart |
| 7,522,963 B2 | 4/2009 | Boyden et al. |
| 7,536,232 B2 | 5/2009 | Boyden et al. |
| 7,577,483 B2 | 8/2009 | Fan et al. |
| 7,587,253 B2 | 9/2009 | Rawlings et al. |
| 7,591,135 B2 | 9/2009 | Stewart |
| 7,599,749 B2 | 10/2009 | Sayyarrodsari et al. |
| 7,599,750 B2 | 10/2009 | Piche |
| 7,603,185 B2 | 10/2009 | Stewart et al. |
| 7,603,226 B2 | 10/2009 | Henein |
| 7,627,843 B2 | 12/2009 | Dozorets et al. |
| 7,630,868 B2 | 12/2009 | Turner et al. |
| 7,634,323 B2 | 12/2009 | Vermillion et al. |
| 7,634,417 B2 | 12/2009 | Boyden et al. |
| 7,650,780 B2 | 1/2010 | Hall |
| 7,668,704 B2 | 2/2010 | Perchanok et al. |
| 7,676,318 B2 | 3/2010 | Allain |
| 7,698,004 B2 | 4/2010 | Boyden et al. |
| 7,702,519 B2 | 4/2010 | Boyden et al. |
| 7,712,139 B2 | 5/2010 | Westendorf et al. |
| 7,721,030 B2 | 5/2010 | Fuehrer et al. |
| 7,725,199 B2 | 5/2010 | Brackney et al. |
| 7,734,291 B2 | 6/2010 | Mazzara, Jr. |
| 7,738,975 B2 | 6/2010 | Denison et al. |
| 7,743,606 B2 | 6/2010 | Havelena et al. |
| 7,748,217 B2 | 7/2010 | Muller |
| 7,752,840 B2 | 7/2010 | Stewart |
| 7,765,792 B2 | 8/2010 | Rhodes et al. |
| 7,779,680 B2 | 8/2010 | Sasaki et al. |
| 7,793,489 B2 | 9/2010 | Wang et al. |
| 7,798,938 B2 | 9/2010 | Matsubara et al. |
| 7,808,371 B2 | 10/2010 | Blanchet et al. |
| 7,813,884 B2 | 10/2010 | Chu et al. |
| 7,826,909 B2 | 11/2010 | Attarwala |
| 7,831,318 B2 | 11/2010 | Bartee et al. |
| 7,840,287 B2 | 11/2010 | Wojsznis et al. |
| 7,844,351 B2 | 11/2010 | Piche |
| 7,844,352 B2 | 11/2010 | Vouzis et al. |
| 7,846,299 B2 | 12/2010 | Backstrom et al. |
| 7,850,104 B2 | 12/2010 | Havlena et al. |
| 7,856,966 B2 | 12/2010 | Saitoh |
| 7,860,586 B2 | 12/2010 | Boyden et al. |
| 7,861,518 B2 | 1/2011 | Federle |
| 7,862,771 B2 | 1/2011 | Boyden et al. |
| 7,877,239 B2 | 1/2011 | Grichnik et al. |
| 7,878,178 B2 | 2/2011 | Stewart et al. |
| 7,891,669 B2 | 2/2011 | Araujo et al. |
| 7,904,280 B2 | 3/2011 | Wood |
| 7,905,103 B2 | 3/2011 | Larsen et al. |
| 7,907,769 B2 | 3/2011 | Sammak et al. |
| 7,925,399 B2 | 4/2011 | Comeau |
| 7,930,044 B2 | 4/2011 | Attarwala |
| 7,933,849 B2 | 4/2011 | Bartee et al. |
| 7,958,730 B2 | 6/2011 | Stewart et al. |
| 7,970,482 B2 | 6/2011 | Srinivasan et al. |
| 7,987,145 B2 | 7/2011 | Baramov |
| 7,996,140 B2 | 8/2011 | Stewart et al. |
| 8,001,767 B2 | 8/2011 | Kakuya et al. |
| 8,019,911 B2 | 9/2011 | Dressler et al. |
| 8,025,167 B2 | 9/2011 | Schneider et al. |
| 8,032,235 B2 | 10/2011 | Sayyar-Rodsari |
| 8,046,089 B2 | 10/2011 | Renfro et al. |
| 8,046,090 B2 | 10/2011 | MacArthur et al. |
| 8,060,290 B2 | 11/2011 | Stewart et al. |
| 8,078,291 B2 | 12/2011 | Pekar et al. |
| 8,108,790 B2 | 1/2012 | Morrison, Jr. et al. |
| 8,109,255 B2 | 2/2012 | Stewart et al. |
| 8,121,818 B2 | 2/2012 | Gorinevsky |
| 8,145,329 B2 | 3/2012 | Pekar et al. |
| 8,146,850 B2 | 4/2012 | Havlena et al. |
| 8,157,035 B2 | 4/2012 | Whitney et al. |
| 8,185,217 B2 | 5/2012 | Thiele |
| 8,197,753 B2 | 6/2012 | Boyden et al. |
| 8,200,346 B2 | 6/2012 | Thiele |
| 8,209,963 B2 | 7/2012 | Kesse et al. |
| 8,229,163 B2 | 7/2012 | Coleman et al. |
| 8,245,501 B2 | 8/2012 | He et al. |
| 8,246,508 B2 | 8/2012 | Matsubara et al. |
| 8,265,854 B2 | 9/2012 | Stewart et al. |
| 8,281,572 B2 | 10/2012 | Chi et al. |
| 8,295,951 B2 | 10/2012 | Crisalle et al. |
| 8,311,653 B2 | 11/2012 | Zhan et al. |
| 8,312,860 B2 | 11/2012 | Yun et al. |
| 8,316,235 B2 | 11/2012 | Boehl et al. |
| 8,360,040 B2 | 1/2013 | Stewart et al. |
| 8,370,052 B2 | 2/2013 | Lin et al. |
| 8,379,267 B2 | 2/2013 | Mestha et al. |
| 8,396,644 B2 | 3/2013 | Kabashima et al. |
| 8,402,268 B2 | 3/2013 | Dierickx |
| 8,418,441 B2 | 4/2013 | He et al. |
| 8,453,431 B2 | 6/2013 | Wang et al. |
| 8,473,079 B2 | 6/2013 | Havlena |
| 8,478,506 B2 | 7/2013 | Grichnik et al. |
| RE44,452 E | 8/2013 | Stewart et al. |
| 8,504,175 B2 | 8/2013 | Pekar et al. |
| 8,505,278 B2 | 8/2013 | Farrell et al. |
| 8,543,170 B2 | 9/2013 | Mazzara, Jr. et al. |
| 8,555,613 B2 | 10/2013 | Wang et al. |
| 8,571,689 B2 | 10/2013 | Macharia et al. |
| 8,596,045 B2 | 12/2013 | Tuomivaara et al. |
| 8,620,461 B2 | 12/2013 | Kihas |
| 8,634,940 B2 | 1/2014 | Macharia et al. |
| 8,639,925 B2 | 1/2014 | Schuetze |
| 8,649,884 B2 | 2/2014 | MacArthur et al. |
| 8,649,961 B2 | 2/2014 | Hawkins et al. |
| 8,667,288 B2 | 3/2014 | Yavuz |
| 8,694,197 B2 | 4/2014 | Rajagopalan et al. |
| 8,700,291 B2 | 4/2014 | Herrmann |
| 8,751,241 B2 | 6/2014 | Oesterling et al. |
| 8,762,026 B2 | 6/2014 | Wolfe et al. |
| 8,763,377 B2 | 7/2014 | Yacoub |
| 8,768,996 B2 | 7/2014 | Shokrollahi et al. |
| 8,813,690 B2 | 8/2014 | Kumar et al. |
| 8,825,243 B2 | 9/2014 | Yang et al. |
| 8,839,967 B2 | 9/2014 | Schneider et al. |
| 8,867,746 B2 | 10/2014 | Ceskutti et al. |
| 8,892,221 B2 | 11/2014 | Kram et al. |
| 8,899,018 B2 | 12/2014 | Frazier et al. |
| 8,904,760 B2 | 12/2014 | Mital |
| 8,983,069 B2 | 3/2015 | Merchan et al. |
| 9,100,193 B2 | 8/2015 | Newsome et al. |
| 9,141,996 B2 | 9/2015 | Christensen et al. |
| 9,170,573 B2 | 10/2015 | Kihas |
| 9,175,595 B2 | 11/2015 | Ceynow et al. |
| 9,223,301 B2 | 12/2015 | Stewart et al. |
| 9,243,576 B2 | 1/2016 | Yu et al. |
| 9,253,200 B2 | 2/2016 | Schwarz et al. |
| 9,325,494 B2 | 4/2016 | Boehl |
| 9,367,701 B2 | 6/2016 | Merchan et al. |
| 9,367,968 B2 | 6/2016 | Giraud et al. |
| 9,483,881 B2 | 11/2016 | Comeau et al. |
| 9,560,071 B2 | 1/2017 | Ruvio et al. |
| 9,779,742 B2 | 10/2017 | Newsome, Jr. |
| 2002/0112469 A1 | 8/2002 | Kanazawa et al. |
| 2003/0029233 A1 | 2/2003 | Ting et al. |
| 2004/0006973 A1 | 1/2004 | Makki et al. |
| 2004/0086185 A1 | 5/2004 | Sun |
| 2004/0144082 A1 | 7/2004 | Mianzo et al. |
| 2004/0199481 A1 | 10/2004 | Hartman et al. |
| 2004/0226287 A1 | 11/2004 | Edgar et al. |
| 2005/0171667 A1 | 8/2005 | Morita |
| 2005/0187643 A1 | 8/2005 | Sayyar-Rodsari et al. |
| 2005/0193739 A1 | 9/2005 | Brunell et al. |
| 2005/0210868 A1 | 9/2005 | Funabashi |

(56) References Cited

U.S. PATENT DOCUMENTS

| | | |
|---|---|---|
| 2006/0047607 A1 | 3/2006 | Boyden et al. |
| 2006/0111881 A1 | 5/2006 | Jackson |
| 2006/0137347 A1 | 6/2006 | Stewart et al. |
| 2006/0168945 A1 | 8/2006 | Samad et al. |
| 2006/0185626 A1 | 8/2006 | Allen et al. |
| 2006/0212140 A1 | 9/2006 | Brackney |
| 2007/0144149 A1 | 6/2007 | Kolavennu et al. |
| 2007/0156259 A1 | 7/2007 | Baramov et al. |
| 2007/0240213 A1 | 10/2007 | Karam et al. |
| 2007/0261648 A1 | 11/2007 | Reckels et al. |
| 2007/0275471 A1 | 11/2007 | Coward |
| 2008/0010973 A1 | 1/2008 | Gimbres |
| 2008/0103747 A1 | 5/2008 | Macharia et al. |
| 2008/0132178 A1 | 6/2008 | Chatterjee et al. |
| 2008/0208778 A1 | 8/2008 | Sayyar-Rodsari et al. |
| 2008/0289605 A1 | 11/2008 | Ito |
| 2009/0172416 A1 | 7/2009 | Bosch et al. |
| 2009/0312998 A1 | 12/2009 | Berckmans et al. |
| 2010/0122523 A1 | 5/2010 | Vosz |
| 2010/0126481 A1 | 5/2010 | Willi et al. |
| 2010/0131181 A1 | 5/2010 | Herrmann |
| 2010/0300069 A1 | 12/2010 | Herrmann et al. |
| 2011/0056265 A1 | 3/2011 | Yacoub |
| 2011/0060424 A1 | 3/2011 | Havlena |
| 2011/0125295 A1 | 5/2011 | Bednasch et al. |
| 2011/0131017 A1 | 6/2011 | Cheng et al. |
| 2011/0167025 A1 | 7/2011 | Danai et al. |
| 2011/0173315 A1 | 7/2011 | Aguren |
| 2011/0264353 A1 | 10/2011 | Atkinson et al. |
| 2011/0270505 A1 | 11/2011 | Chaturvedi et al. |
| 2012/0024089 A1 | 2/2012 | Couey et al. |
| 2012/0109620 A1 | 5/2012 | Gaikwad et al. |
| 2012/0174187 A1 | 7/2012 | Argon et al. |
| 2013/0024069 A1 | 1/2013 | Wang et al. |
| 2013/0067894 A1 | 3/2013 | Stewart et al. |
| 2013/0111878 A1 | 5/2013 | Pachner et al. |
| 2013/0111905 A1 | 5/2013 | Pekar et al. |
| 2013/0131954 A1 | 5/2013 | Yu et al. |
| 2013/0131956 A1 | 5/2013 | Thibault et al. |
| 2013/0158834 A1 | 6/2013 | Wagner et al. |
| 2013/0204403 A1 | 8/2013 | Zheng et al. |
| 2013/0242706 A1 | 9/2013 | Newsome, Jr. |
| 2013/0326232 A1 | 12/2013 | Lewis et al. |
| 2013/0326630 A1 | 12/2013 | Argon |
| 2013/0338900 A1 | 12/2013 | Ardanese et al. |
| 2014/0032189 A1 | 1/2014 | Hehle et al. |
| 2014/0034460 A1 | 2/2014 | Chou |
| 2014/0171856 A1 | 6/2014 | McLaughlin et al. |
| 2014/0251287 A1* | 9/2014 | Takezoe .............. F02D 41/0052 123/568.11 |
| 2014/0258736 A1 | 9/2014 | Merchan et al. |
| 2014/0270163 A1 | 9/2014 | Merchan |
| 2014/0316683 A1 | 10/2014 | Whitney et al. |
| 2014/0318216 A1 | 10/2014 | Singh |
| 2014/0343713 A1 | 11/2014 | Ziegler et al. |
| 2014/0358254 A1 | 12/2014 | Chu et al. |
| 2015/0090236 A1* | 4/2015 | Chen .................. F02D 41/0077 123/568.12 |
| 2015/0121071 A1 | 4/2015 | Schwarz et al. |
| 2015/0198104 A1* | 7/2015 | Haehara ............. F02D 41/0062 123/445 |
| 2015/0275783 A1 | 10/2015 | Wong et al. |
| 2015/0321642 A1 | 11/2015 | Schwepp et al. |
| 2015/0324576 A1 | 11/2015 | Quirant et al. |
| 2015/0334093 A1 | 11/2015 | Mueller |
| 2015/0354877 A1 | 12/2015 | Bums et al. |
| 2016/0003180 A1 | 1/2016 | McNulty et al. |
| 2016/0043832 A1 | 2/2016 | Ahn et al. |
| 2016/0108732 A1 | 4/2016 | Huang et al. |
| 2016/0127357 A1 | 5/2016 | Zibuschka et al. |
| 2016/0216699 A1 | 7/2016 | Pekar et al. |
| 2016/0239593 A1 | 8/2016 | Pekar et al. |
| 2016/0259584 A1 | 9/2016 | Schlottmann et al. |
| 2016/0312722 A1* | 10/2016 | Nogi ................... F02D 41/0275 |
| 2016/0330204 A1 | 11/2016 | Baur et al. |
| 2016/0344705 A1 | 11/2016 | Stumpf et al. |
| 2016/0362838 A1 | 12/2016 | Badwe et al. |
| 2016/0365977 A1 | 12/2016 | Boutros et al. |
| 2017/0031332 A1 | 2/2017 | Santin |
| 2017/0048063 A1 | 2/2017 | Mueller |
| 2017/0126701 A1 | 5/2017 | Glas et al. |
| 2017/0218860 A1 | 8/2017 | Pachner et al. |
| 2017/0300713 A1 | 10/2017 | Fan et al. |
| 2017/0306871 A1 | 10/2017 | Fuxman et al. |

FOREIGN PATENT DOCUMENTS

| | | |
|---|---|---|
| DE | 19628796 C1 | 10/1997 |
| DE | 10219382 A1 | 11/2002 |
| DE | 102009016509 A1 | 10/2010 |
| DE | 102011103346 A1 | 8/2012 |
| EP | 0301527 A2 | 2/1989 |
| EP | 0877309 B1 | 6/2000 |
| EP | 1134368 A2 | 9/2001 |
| EP | 1148228 A2 | 10/2001 |
| EP | 1180583 A2 | 2/2002 |
| EP | 1221544 A2 | 7/2002 |
| EP | 1225490 A2 | 7/2002 |
| EP | 1245811 A2 | 10/2002 |
| EP | 1273337 A1 | 1/2003 |
| EP | 0950803 B1 | 9/2003 |
| EP | 1416138 A2 | 5/2004 |
| EP | 1420153 A2 | 5/2004 |
| EP | 1447727 A2 | 8/2004 |
| EP | 1498791 A1 | 1/2005 |
| EP | 1425642 B1 | 11/2005 |
| EP | 1686251 A1 | 8/2006 |
| EP | 1399784 B1 | 10/2007 |
| EP | 2107439 A1 | 10/2009 |
| EP | 2146258 A1 | 1/2010 |
| EP | 2221465 A1 | 8/2010 |
| EP | 1794339 B1 | 7/2011 |
| EP | 1529941 B1 | 11/2011 |
| EP | 2339153 A1 | 12/2011 |
| EP | 2543845 A1 | 1/2013 |
| EP | 2551480 A1 | 1/2013 |
| EP | 2589779 A2 | 5/2013 |
| EP | 2617975 A1 | 7/2013 |
| EP | 2267559 B1 | 1/2014 |
| EP | 2853723 A1 | 4/2015 |
| EP | 2919079 A2 | 9/2015 |
| FR | 2856738 A1 | 6/2004 |
| FR | 2919024 A1 | 1/2009 |
| JP | 59190433 A | 10/1984 |
| JP | 2010282618 A | 12/2010 |
| JP | 201637932 A | 3/2016 |
| WO | 0144629 A2 | 6/2001 |
| WO | 0169056 A1 | 9/2001 |
| WO | 0232552 A1 | 4/2002 |
| WO | 02097540 A1 | 12/2002 |
| WO | 02101208 A1 | 12/2002 |
| WO | 03023538 A2 | 3/2003 |
| WO | 03048533 A1 | 6/2003 |
| WO | 03065135 A1 | 8/2003 |
| WO | 03078816 A1 | 9/2003 |
| WO | 03102394 A1 | 12/2003 |
| WO | 2004027230 A1 | 4/2004 |
| WO | 2006021437 A1 | 3/2006 |
| WO | 2007078907 A2 | 7/2007 |
| WO | 2008033800 A2 | 3/2008 |
| WO | 2008115911 A1 | 9/2008 |
| WO | 2012076838 A2 | 6/2012 |
| WO | 2013119665 A1 | 8/2013 |
| WO | 2014165439 A2 | 10/2014 |
| WO | 2016053194 A1 | 4/2016 |

OTHER PUBLICATIONS

"Chapter 14: Pollutant Formation," Fluent Manual, Release 15.0, Chapter 14, pp. 313-345, prior to Jan. 29, 2016.

"Chapter 21, Modeling Pollutant Formation," Fluent Manual, Release 12.0, Chapter 21, pp. 21-1-21-54, Jan. 30, 2009.

(56) References Cited

OTHER PUBLICATIONS

"J1979 E/E Diagnostic Test Modules," Proposed Regulation, Vehicle E.E. System Diagnostic Standards Committee, 1 page, Sep. 28, 2010.
"MicroZed Zynq Evaluation and Development and System on Module, Hardware User Guide," Avnet Electronics Marketing, Version 1.6, Jan. 22, 2015.
"Model Predictive Control Toolbox Release Notes," The Mathworks, 24 pages, Oct. 2008.
"Model Predictive Control," Wikipedia, pp. 1-5, Jan. 22, 2009. http://en.wikipedia.org/w/index.php/title=Special:Book&bookcmd=download&collecton_id=641cd1b5da77cc22&writer=rl&return_to=Model predictive control, retrieved Nov. 20, 2012.
"MPC Implementation Methods for the Optimization of the Response of Control Valves to Reduce Variability," Advanced Application Note 002, Rev. A, 10 pages, 2007.
"SCR, 400-csi Coated Catalyst," Leading NOx Control Technologies Status Summary, 1 page prior to Feb. 2, 2005.
Actron, "Elite AutoScanner Kit—Enhanced OBD I & II Scan Tool, OBD 1300," Downloaded from https://actron.com/content/elite-autoscanner-kit-enhanced-obd-i-and-obd-ii-scan-tool?utm_ . . . , 5 pages, printed Sep. 27, 2016.
Advanced Petroleum-Based Fuels-Diesel Emissions Control (APBF-DEC) Project, "Quarterly Update," No. 7, 6 pages, Fall 2002.
Allanson, et al., "Optimizing the Low Temperature Performance and Regeneration Efficiency of the Continuously Regenerating Diesel Particulate Filter System," SAE Paper No. 2002-01-0428, 8 pages, Mar. 2002.
Amstuz, et al., "EGO Sensor Based Robust Output Control of EGR in Diesel Engines," IEEE TCST, vol. 3, No. 1, 12 pages, Mar. 1995.
Andersson et al., "A Predictive Real Time NOx Model for Conventional and Partially Premixed Diesel Combustion," SAE International 2006-01-3329, 10 pages, 2006.
Andersson et al., "A Real Time NOx Model for Conventional and Partially Premixed Diesel Combustion," SAE Technical Paper Series 2006-01-0195, 2006 SAE World Congress, 13 pages, Apr. 3-6, 2006.
Arregle et al., "On Board NOx Prediction in Diesel Engines: A Physical Approach," Automotive Model Predictive Control, Models Methods and Applications, Chapter 2, 14 pages, 2010.
Asprion, "Optimal Control of Diesel Engines," PHD Thesis, Diss ETH No. 21593, 436 pages, 2013.
Assanis et al., "A Predictive Ignition Delay Correlation Under Steady-State and Transient Operation of a Direct Injection Diesel Engine," ASME, Journal of Engineering for Gas Turbines and Power, vol. 125, pp. 450-457, Apr. 2003.
Axehill et al., "A Dual Gradiant Projection Quadratic Programming Algorithm Tailored for Model Predictive Control," Proceedings of the 47th IEEE Conference on Decision and Control, Cancun Mexico, pp. 3057-3064, Dec. 9-11, 2008.
Axehill et al., "A Dual Gradient Projection Quadratic Programming Algorithm Tailored for Mixed Integer Predictive Control," Technical Report from Linkopings Universitet, Report No. Li-Th-ISY-R-2833, 58 pages, Jan. 31, 2008.
Baffi et al., "Non-Linear Model Based Predictive Control Through Dynamic Non-Linear Partial Least Squares," Trans IChemE, vol. 80, Part A, pp. 75-86, Jan. 2002.
Bako et al., "A Recursive Identification Algorithm for Switched Linear/Affine Models," Nonlinear Analysis: Hybrid Systems, vol. 5, pp. 242-253, 2011.
Barba et al., "A Phenomenological Combustion Model for Heat Release Rate Prediction in High-Speed DI Diesel Engines with Common Rail Injection," SAE Technical Paper Series 2000-01-2933, International Fall Fuels and Lubricants Meeting Exposition, 15 pages, Oct. 16-19, 2000.
Bemporad et al., "Model Predictive Control Toolbox 3, User's Guide," Matlab Mathworks, 282 pages, 2008.
Bemporad et al., "The Explicit Linear Quadratic Regulator for Constrained Systems," Automatica, 38, pp. 3-20, 2002.
Bemporad, "Model Predictive Control Based on Linear Programming—The Explicit Solution," IEEE Transactions on Automatic Control, vol. 47, No. 12, pp. 1974-1984, Dec. 2002.
Bemporad, "Model Predictive Control Design: New Trends and Tools," Proceedings of the 45th IEEE Conference on Decision & Control, pp. 6678-6683, Dec. 13-15, 2006.
Bemporad, et al., "Explicit Model Predictive Control," 1 page, prior to Feb. 2, 2005.
Bertsekas, "On the Goldstein-Levitin-Polyak Gradient Projection Method," IEEE Transactions on Automatic Control, vol. AC-21, No. 2, pp. 174-184, Apr. 1976.
Bertsekas, "Projected Newton Methods for Optimization Problems with Simple Constraints," SIAM J. Control and Optimization, vol. 20, No. 2, pp. 221-246, Mar. 1982.
Blanco-Rodriguez, "Modelling and Observation of Exhaust Gas Concentrations for Diesel Engine Control," PHD Dissertation, 242 pages, Sep. 2013.
Blue Streak Electronics Inc., "Ford Modules," 1 page, May 12, 2010.
Borrelli et al., "An MPC/Hybrid System Approach to Traction Control," IEEE Transactions on Control Systems Technology, vol. 14, No. 3, pp. 541-553, May 2006.
Borrelli, "Constrained Optimal Control of Linear and Hybrid Systems," Lecture Notes in Control and Information Sciences, vol. 290, 2003.
Borrelli, "Discrete Time Constrained Optimal Control," A Dissertation Submitted to the Swiss Federal Institute of Technology (ETH) Zurich, Diss. ETH No. 14666, 232 pages, Oct. 9, 2002.
Bourn et al., "Advanced Compressor Engine Controls to Enhance Operation, Reliability and Integrity," Southwest Research Institute, DOE Award No. DE-FC26-03NT41859, SwRI Project No. 03.10198, 60 pages, Mar. 2004.
Catalytica Energy Systems, "Innovative NOx Reduction Solutions for Diesel Engines," 13 pages, 3rd Quarter, 2003.
Charalampidis et al., "Computationally Efficient Kalman Filtering for a Class of Nonlinear Systems," IEEE Transactions on Automatic Control, vol. 56, No. 3, pp. 483-491, Mar. 2011.
Chatterjee, et al. "Catalytic Emission Control for Heavy Duty Diesel Engines," JM, 46 pages, prior to Feb. 2, 2005.
Chew, "Sensor Validation Scheme with Virtual NOx Sensing for Heavy Duty Diesel Engines," Master's Thesis, 144 pages, 2007.
European Search Report for EP Application No. 11167549.2 dated Nov. 27, 2012.
European Search Report for EP Application No. 12191156.4-1603 dated Feb. 9, 2015.
European Search Report for EP Application No. EP 10175270.7-2302419 dated Jan. 16, 2013.
European Search Report for EP Application No. EP 15152957.5-1807 dated Feb. 10, 2015.
Extended European Search Report for EP Application No. 15155295.7-1606, dated Aug. 4, 2015.
Extended European Search Report for EP Application No. 15179435.1, dated Apr. 1, 2016.
De Oliveira, "Constraint Handling and Stability Properties of Model Predictive Control," Carnegie Institute of Technology, Department of Chemical Engineering, Paper 197, 64 pages, Jan. 1, 1993.
De Schutter et al., "Model Predictive Control for Max-Min-Plus-Scaling Systems," Proceedings of the 2001 American Control Conference, Arlington, Va, pp. 319-324, Jun. 2001.
Delphi, Delphi Diesel NOx Trap (DNT), 3 pages, Feb. 2004.
Diehl et al., "Efficient Numerical Methods for Nonlinear MPC and Moving Horizon Estimation," Int. Workshop on Assessment and Future Directions of NMPC, 24 pages, Pavia, Italy, Sep. 5-9, 2008.
Ding, "Characterising Combustion in Diesel Engines, Using Parameterised Finite Stage Cylinder Process Models," 281 pages, Dec. 21, 2011.
Docquier et al., "Combustion Control and Sensors: a Review," Progress in Energy and Combustion Science, vol. 28, pp. 107-150, 2002.
Dunbar, "Model Predictive Control: Extension to Coordinated Multi-Vehicle Formations and Real-Time Implementation," CDS Technical Report 01-016, 64 pages, Dec. 7, 2001.

(56) References Cited

OTHER PUBLICATIONS

Egnell, "Combustion Diagnostics by Means of Multizone Heat Release Analysis and NO Calculation," SAE Technical Paper Series 981424, International Spring Fuels and Lubricants Meeting and Exposition, 22 pages, May 4-6, 1998.
Ericson, "NOx Modelling of a Complete Diesel Engine/SCR System," Licentiate Thesis, 57 pages, 2007.
Finesso et al., "Estimation of the Engine-Out NO2/NOx Ration in a Euro VI Diesel Engine," SAE International 2013-01-0317, 15 pages, Apr. 8, 2013.
Fleming, "Overview of Automotive Sensors," IEEE Sensors Journal, vol. 1, No. 4, pp. 296-308, Dec. 2001.
Ford Motor Company, "2012 My OBD System Operation Summary for 6.7L Diesel Engines," 149 pages, Apr. 21, 2011.
Formentin et al., "NOx Estimation in Diesel Engines via In-Cylinder Pressure Measurement," IEEE Transactions on Control Systems Technology, vol. 22, No. 1, pp. 396-403, Jan. 2014.
Galindo, "An On-Engine Method for Dynamic Characterisation of NOx Concentration Sensors," Experimental Thermal and Fluid Science, vol. 35, pp. 470-476, 2011.
Gamma Technologies, "Exhaust Aftertreatment with GT-Suite," 2 pages, Jul. 17, 2014.
GM "Advanced Diesel Technology and Emissions," powertrain technologies—engines, 2 pages, prior to Feb. 2, 2005.
Goodwin, "Researchers Hack A Corvette's Brakes via Insurance Black Box," Downloaded from http://www.cnet.com/roadshow/news/researchers-hack-a-corvettes-brakes-via-insurance-black-box/, 2 pages, Aug. 2015.
Greenberg, "Hackers Remotely Kill a Jeep on the Highway—With Me in It," Downloaded from http://www.wired.com/2015/07/hackers-remotely-kill-jeep-highway/, 24 pages, Jul. 21, 2015.
Guardiola et al., "A Bias Correction Method for Fast Fuel-to-Air Ratio Estimation in Diesel Engines," Proceedings of the Institution of Mechanical Engineers, Part D: Journal of Automobile Engineering, vol. 227, No. 8, pp. 1099-1111, 2013.
Guardiola et al., "A Computationally Efficient Kalman Filter Based Estimator for Updating Look-Up Tables Applied to NOx Estimation in Diesel Engines," Control Engineering Practice, vol. 21, pp. 1455-1468.
Guerreiro et al., "Trajectory Tracking Nonlinear Model Predictive Control for Autonomous Surface Craft," Proceedings of the European Control Conference, Budapest, Hungary, 6 pages, Aug. 2009.
Guzzella et al., "Introduction to Modeling and Control of Internal Combustion Engine Systems," 303 pages, 2004.
Guzzella, et al., "Control of Diesel Engines," IEEE Control Systems Magazine, pp. 53-71, Oct. 1998.
Hahlin, "Single Cylinder ICE Exhaust Optimization," Master's Thesis, retrieved from https://pure.ltu.se/portal/files/44015424/LTU-EX-2013-43970821.pdf, 50 pages, Feb. 1, 2014.
Hammacher Schlemmer, "The Windshield Heads Up Display," Catalog, p. 47, prior to Apr. 26, 2016.
Havelena, "Componentized Architecture for Advanced Process Management," Honeywell International, 42 pages, 2004.
Heywood, "Pollutant Formation and Control," Internal Combustion Engine Fundamentals, pp. 567-667, 1988.
Hiranuma, et al., "Development of DPF System for Commercial Vehicle—Basic Characteristic and Active Regeneration Performance," SAE Paper No. 2003-01-3182, Mar. 2003.
Hirsch et al., "Dynamic Engine Emission Models," Automotive Model Predictive Control, Chapter 5, 18 pages, LNCIS 402, 2012.
Hirsch et al., "Grey-Box Control Oriented Emissions Models," The International Federation of Automatic Control (IFAC), Proceedings of the 17th World Congress, pp. 8514-8519, Jul. 6-11, 2008.
Hockerdal, "EKF-based Adaptation of Look-Up Tables with an Air Mass-Flow Sensor Application," Control Engineering Practice, vol. 19, 12 pages, 2011.
Honeywell, "Profit Optimizer A Distributed Quadratic Program (DQP) Concepts Reference," 48 pages, prior to Feb. 2, 2005.
http://nexceris.com/news/nextech-materials/, "NEXTECH Materials is Now NEXCERIS," 7 pages, printed Oct. 4, 2016.
http://www.arb.ca.gov/msprog/obdprog/hdobdreg.htm, "Heavy-Duty OBD Regulations and Rulemaking," 8 pages, printed Oct. 4, 2016.
http://www.not2fast.wryday.com/turbo/glossary/turbo_glossary.shtml, "Not2Fast: Turbo Glossary," 22 pages, printed Oct. 1, 2004.
http://www.tai-cwv.com/sbl106.0.html, "Technical Overview—Advanced Control Solutions," 6 pages, printed Sep. 9, 2004.
https://www.dieselnet.com/standards/us/obd.php, "Emission Standards: USA: On-Board Diagnostics," 6 pages, printed Oct. 3, 2016.
https://www.en.wikipedia.org/wiki/Public-key_cryptography, "Public-Key Cryptography," 14 pages, printed Feb. 26, 2016.
Ishida et al., "An Analysis of the Added Water Effect on NO Formation in D.I. Diesel Engines," SAE Technical Paper Series 941691, International Off-Highway and Power-Plant Congress and Exposition, 13 pages, Sep. 12-14, 1994.
Ishida et al., "Prediction of NOx Reduction Rate Due to Port Water Injection in a DI Diesel Engine," SAE Technical Paper Series 972961, International Fall Fuels and Lubricants Meeting and Exposition, 13 pages, Oct. 13-16, 1997.
Jensen, "The 13 Monitors of an OBD System," http://www.oemoffhighway.com/article/1 0855512/the-13-monito . . . , 3 pages, printed Oct. 3, 2016.
Johansen et al., "Hardware Architecture Design for Explicit Model Predictive Control," Proceedings of ACC, 6 pages, 2006.
Johansen et al., "Hardware Synthesis of Explicit Model Predictive Controllers," IEEE Transactions on Control Systems Technology, vol. 15, No. 1, Jan. 2007.
Jonsson, "Fuel Optimized Predictive Following in Low Speed Conditions," Master's Thesis, 46 pages, Jun. 28, 2003.
Kelly, et al., "Reducing Soot Emissions from Diesel Engines Using One Atmosphere Uniform Glow Discharge Plasma," SAE Paper No. 2003-01-1183, Mar. 2003.
Keulen et al., "Predictive Cruise Control in Hybrid Electric Vehicles," World Electric Journal, vol. 3, ISSN 2032-6653, 11 pages, May 2009.
Khair et al., "Emission Formation in Diesel Engines," Downloaded from https://www.dieselnelcom/tech/diesel_emiform.php, 33 pages, printed Oct. 14, 2016.
Kihas et al., "Chapter 14, Diesel Engine SCR Systems: Modeling Measurements and Control," Catalytic Reduction Technology (book), Part 1, Chapter 14, prior to Jan. 29, 2016.
Kolmanovsky et al., "Issues in Modeling and Control of Intake Flow in Variable Geometry Turbocharged Engines", 18th IFIP Conf. System Modeling and Optimization, pp. 436-445, Jul. 1997.
Krause et al., "Effect of Inlet Air Humidity and Temperature on Diesel Exhaust Emissions," SAE International Automotive Engineering Congress, 8 pages, Jan. 8-12, 1973.
Kulhavy et al. "Emerging Technologies for Enterprise Optimization in the Process Industries," Honeywell, 12 pages, Dec. 2000.
Lavoie et al., "Experimental and Theoretical Study of Nitric Oxide Formation in Internal Combustion Engines," Combustion Science and Technology, vol. 1, pp. 313-326, 1970.
Locker, et al., "Diesel Particulate Filter Operational Characterization," Corning Incorporated, 10 pages, prior to Feb. 2, 2005.
Lu, "Challenging Control Problems and Engineering Technologies in Enterprise Optimization," Honeywell Hi-Spec Solutions, 30 pages, Jun. 4-6, 2001.
Van Keulen et al., "Predictive Cruise Control in Hybrid Electric Vehicles," World Electric Vehicle Journal vol. 3, ISSN 2032-6653, pp. 1-11, 2009.
Vdo, "UniNOx-Sensor Specification," Continental Trading GmbH, 2 pages, Aug. 2007.
Vereschaga et al., "Piecewise Affine Modeling of NOx Emission Produced by a Diesel Engine," 2013 European Control Conference (ECC), pp. 2000-2005, Jul. 17-19, 2013.
Wahlstrom et al., "Modelling Diesel Engines with a Variable-Geometry Turbocharger and Exhaust Gas Recirculation by Optimization of Model Parameters for Capturing Non-Linear System Dynamics," (Original Publication) Proceedings of the Institution of Mechanical Engineers, Part D, Journal of Automobile Engineering, vol. 225, No. 7, 28 pages, 2011.

(56) References Cited

OTHER PUBLICATIONS

Wang et al., "Fast Model Predictive Control Using Online Optimization," Proceedings of the 17th World Congress, the International Federation of Automatic Control, Seoul, Korea, pp. 6974-6979, Jul. 6-11, 2008.
Wang et al., "PSO-Based Model Predictive Control for Nonlinear Processes," Advances in Natural Computation, Lecture Notes in Computer Science, vol. 3611/2005, 8 pages, 2005.
Wang et al., "Sensing Exhaust NO2 Emissions Using the Mixed Potential Principal," SAE 2014-01-1487, 7 pages, Apr. 1, 2014.
Wilhelmsson et al., "A Fast Physical NOx Model Implemented on an Embedded System," Proceedings of the IFAC Workshop on Engine and Powertrain Control, Simulation and Modeling, pp. 207-215, Nov. 30-Dec. 2, 2009.
Wilhemsson et al., "A Physical Two-Zone NOx Model Intended for Embedded Implementation," SAE 2009-01-1509, 11 pages, 2009.
Winkler et al., "Incorporating Physical Knowledge About the Formation of Nitric Oxides into Evolutionary System Identification," Proceedings of the 20th European Modeling and Simulation Symposium (EMSS), 6 pages, 2008.
Winkler et al., "On-Line Modeling Based on Genetic Programming," 12 pages, International Journal on Intelligent Systems Technologies and Applications 2, 2007.
Winkler et al., "Using Genetic Programming in Nonlinear Model Identification," 99 pages, prior to Jan. 29, 2016.
Winkler et al., "Virtual Sensors for Emissions of a Diesel Engine Produced by Evolutionary System Identification," LNCS, vol. 5717, 8 pages, 2009.
Wong, "Care Heavy-Duty OBD Update," California Air Resources Board, SAE OBD TOPTEC, Downloaded from http://www.arb.ca.gov/msprog/obdprog/hdobdreg.htm, 72 pages, Sep. 15, 2005.
Wright, "Applying New Optimization Algorithms to Model Predictive Control," 5th International Conference on Chemical Process Control, 10 pages, 1997.
Yao et al., "The Use of Tunnel Concentration Profile Data to Determine the Ratio of NO2/NOx Directly Emitted from Vehicles," HAL Archives, 19 pages, 2005.
Zaman, "Lincoln Motor Company: Case study 2015 Lincoln MKC," Automotive Electronic Design Fundamentals, Chapter 6, 2015.
Zavala et al., "The Advance-Step NMPC Controller: Optimality, Stability, and Robustness," Automatica, vol. 45, pp. 86-93, 2009.
Zeilinger et al., "Real-Time MPC—Stability Through Robust MPC Design," Joint 48th IEEE Conference on Decision and Control and 28th Chinese Control Conference, Shanghai, P.R. China, pp. 3980-3986, Dec. 16-18, 2009.
Zeldovich, "The Oxidation of Nitrogen in Combustion and Explosions," ACTA Physiochimica U.R.S.S., vol. XX1, No. 4, 53 pages, 1946.
Zelenka, et al., "An Active Regeneration as a Key Element for Safe Particulate Trap Use," SAE Paper No. 2001-0103199, 13 pages, Feb. 2001.
Zhu, "Constrained Nonlinear Model Predictive Control for Vehicle Regulation," Dissertation, Graduate School of the Ohio State University, 125 pages, 2008.
Zhuiykov et al., "Development of Zirconia-Based Potentiometric NOx Sensors for Automotive and Energy Industries in the Early 21st Century: What Are the Prospects for Sensors?", Sensors and Actuators B, vol. 121, pp. 639-651, 2007.
Desantes et al., "Development of NOx Fast Estimate Using NOx Sensor," EAEC 2011 Congress, 2011.
Andersson et al., "Fast Physical NOx Prediction in Diesel Engines, The Diesel Engine: The Low CO2 and Emissions Reduction Challenge," Conference Proceedings, Lyon, 2006.
Winkler, "Evolutionary System Identification—Modern Approaches and Practical Applications," Kepler Universitat Linz, Reihe C: Technik and Naturwissenschaften, Universitatsverlag Rudolf Trauner, 2009.
Smith, "Demonstration of a Fast Response On-Board NOx Sensor for Heavy-Duty Diesel Vehicles," Technical report, Southwest Research Institute Engine and Vehicle Research Division SwRI Project No. 03-02256 Contract No. 98-302, 2000.
Extended European Search Report for EP Application No. 17151521.6, dated Oct. 23, 2017.
Extended European Search Report for EP Application No. 17163452.0, dated Sep. 26, 2017.
Greenberg, "Hackers Cut a Corvette's Brakes via a Common Car Gadget," downloaded from https://www.wired.com2015/08/hackers-cut-corvettes-brakes-v . . . , 14 pages, Aug. 11, 2015, printed Dec. 11, 2017.
http://www.blackpoolcommunications.com/products/alarm-immo . . . , "OBD Security OBD Port Protection—Alarms & Immobilizers . . . ," 1 page, printed Jun. 5, 2017.
http://www.cnbc.com/2016/09/20/chinese-company-hacks-tesla-car-remotely.html, "Chinese Company Hacks Tesla Car Remotely," 3 pages, Sep. 20, 2016.
ISO, "ISO Document No. 13185-2:2015(E)," 3 pages, 2015.
Maciejowski, "Predictive Control with Constraints," Prentice Hall, Pearson Education Limited, 4 pages, 2002.
Manchur et al., "Time Resolution Effects on Accuracy of Real-Time NOx Emissions Measurements," SAE Technical Paper Series 2005-01-0674, 2005 SAE World Congress, 19 pages, Apr. 11-14, 2005.
Mariethoz et al., "Sensorless Explicit Model Predictive Control of the DC-DC Buck Converter with Inductor Current Limitation," IEEE Applied Power Electronics Conference and Exposition, pp. 1710-1715, 2008.
Marjanovic, "Towards a Simplified Infinite Horizon Model Predictive Controller," 6 pages, Proceedings of the 5th Asian Control Conference, 6 pages, Jul. 20-23, 2004.
Mehta, "The Application of Model Predictive Control to Active Automotive Suspensions," 56 pages, May 17, 1996.
Mohammadpour et al., "A Survey on Diagnostics Methods for Automotive Engines," 2011 American Control Conference, pp. 985-990, Jun. 29-Jul. 1, 2011.
Moore, "Living with Cooled-EGR Engines," Prevention Illustrated, 3 pages, Oct. 3, 2004.
Moos, "Catalysts as Sensors—A Promising Novel Approach in Automotive Exhaust Gas Aftertreatment," http://www.mdpi.com/1424-8220/10/7/6773htm, 10 pages, Jul. 13, 2010.
Murayama et al., "Speed Control of Vehicles with Variable Valve Lift Engine by Nonlinear MPC," ICROS-SICE International Joint Conference, pp. 4128-4133, 2009.
National Renewable Energy Laboratory (NREL), "Diesel Emissions Control—Sulfur Effects Project (DECSE) Summary of Reports," U.S. Department of Energy, 19 pages, Feb. 2002.
Olsen, "Analysis and Simulation of the Rate of Heat Release (ROHR) in Diesel Engines," MSc-Assignment, 105 pages, Jun. 2013.
Ortner et al., "MPC for a Diesel Engine Air Path Using an Explicit Approach for Constraint Systems," Proceedings of the 2006 IEEE Conference on Control Applications, Munich Germany, pp. 2760-2765, Oct. 4-6, 2006.
Ortner et al., "Predictive Control of a Diesel Engine Air Path," IEEE Transactions on Control Systems Technology, vol. 15, No. 3, pp. 449-456, May 2007.
Pannocchia et al., "Combined Design of Disturbance Model and Observer for Offset-Free Model Predictive Control," IEEE Transactions on Automatic Control, vol. 52, No. 6, 6 pages, 2007.
Patrinos et al., "A Global Piecewise Smooth Newton Method for Fast Large-Scale Model Predictive Control," Tech Report TR2010-02, National Technical University of Athens, 23 pages, 2010.
Payri et al., "Diesel NOx Modeling with a Reduction Mechanism for the Initial NOx Coming from EGR or Re-Entrained Burned Gases," 2008 World Congress, SAE Technical Paper Series 2008-01-1188, 13 pages, Apr. 14-17, 2008.
Payri et al., "Methodology for Design and Calibration of a Drift Compensation Method for Fuel-to-Air Ratio," SAE International 2012-01-0717, 13 pages, Apr. 16, 2012.
Pipho et al., "NO2 Formation in a Diesel Engine," SAE Technical Paper Series 910231, International Congress and Exposition, 15 pages, Feb. 25-Mar. 1, 1991.
Qin et al., "A Survey of Industrial Model Predictive Control Technology," Control Engineering Practice, 11, pp. 733-764, 2003.

(56) References Cited

OTHER PUBLICATIONS

Querel et al., "Control of an SCR System Using a Virtual NOx Sensor," 7th IFAC Symposium on Advances in Automotive Control, The International Federation of Automotive Control, pp. 9-14, Sep. 4-7, 2013.

Rajamani, "Data-based Techniques to Improve State Estimation in Model Predictive Control," Ph.D. Dissertation, 257 pages, 2007.

Rawlings, "Tutorial Overview of Model Predictive Control," IEEE Control Systems Magazine, pp. 38-52, Jun. 2000.

Ricardo Software, "Powertrain Design at Your Fingertips," retrieved from http://www.ricardo.com/PageFiles/864/WaveFlyerA4_4PP.pdf, 2 pages, downloaded Jul. 27, 2015.

Salvat, et al., "Passenger Car Serial Application of a Particulate Filter System on a Common Rail Direct Injection Engine," SAE Paper No. 2000-01-0473, 14 pages, Feb. 2000.

Santin et al., "Combined Gradient/Newton Projection Semi-Explicit QP Solver for Problems with Bound Constraints," 2 pages, prior to Jan. 29, 2016.

Schauffele et al., "Automotive Software Engineering Principles, Processes, Methods, and Tools," SAE International, 10 pages, 2005.

Schilling et al., "A Real-Time Model for the Prediction of the NOx Emissions in DI Diesel Engines," Proceedings of the 2006 IEEE International Conference on Control Applications, pp. 2042-2047, Oct. 4-7, 2006.

Schilling, "Model-Based Detection and Isolation of Faults in the Air and Fuel Paths of Common-Rail DI Diesel Engines Equipped with a Lambda and a Nitrogen Oxides Sensor," Doctor of Sciences Dissertation, 210 pages, 2008.

Shahzad et al., "Preconditioners for Inexact Interior Point Methods for Predictive Control," 2010 American Control Conference, pp. 5714-5719, Jun. 30-Jul. 2010.

Shamma, et al. "Approximate Set-Valued Observers for Nonlinear Systems," IEEE Transactions on Automatic Control, vol. 42, No. 5, May 1997.

Signer et al., "European Programme on Emissions, Fuels and Engine Technologies (EPEFE)—Heavy Duty Diesel Study," International Spring Fuels and Lubricants Meeting, SAE 961074, May 6-8, 1996.

Soltis, "Current Status of NOx Sensor Development," Workshop on Sensor Needs and Requirements for PEM Fuel Cell Systems and Direct-Injection Engines, 9 pages, Jan. 25-26, 2000.

Stefanopoulou, et al., "Control of Variable Geometry Turbocharged Diesel Engines for Reduced Emissions," IEEE Transactions on Control Systems Technology, vol. 8, No. 4, pp. 733-745, Jul. 2000.

Stewart et al., "A Model Predictive Control Framework for Industrial Turbodiesel Engine Control," Proceedings of the 47th IEEE Conference on Decision and Control, 8 pages, 2008.

Stewart et al., "A Modular Model Predictive Controller for Turbodiesel Problems," First Workshop on Automotive Model Predictive Control, Schloss Muhldorf, Feldkirchen, Johannes Kepler University, Linz, 3 pages, 2009.

Storset et al., "Air Charge Estimation for Turbocharged Diesel Engines," vol. 1 Proceedings of the American Control Conference, 8 pages, Jun. 28-30, 2000.

Stradling et al., "The Influene of Fuel Properties and Injection Timing on the Exhaust Emissions and Fuel Consumption of an Iveco Heavy-Duty Diesel Engine," International Spring Fuels and Lubricants Meeting, SAE 971635, May 5-8, 1997.

Takacs et al., "Newton-Raphson Based Efficient Model Predictive Control Applied on Active Vibrating Structures," Proceeding of the European Control Conference 2009, Budapest, Hungary, pp. 2845-2850, Aug. 23-26, 2009.

The MathWorks, "Model-Based Calibration Toolbox 2.1 Calibrate complex powertrain systems," 4 pages, prior to Feb. 2, 2005.

The MathWorks, "Model-Based Calibration Toolbox 2.1.2," 2 pages, prior to Feb. 2, 2005.

Theiss, "Advanced Reciprocating Engine System (ARES) Activities at the Oak Ridge National Lab (ORNL), Oak Ridge National Laboratory," U.S. Department of Energy, 13 pages, Apr. 14, 2004.

Tondel et al., "An Algorithm for Multi-Parametric Quadratic Programming and Explicit MPC Solutions," Automatica, 39, pp. 489-497, 2003.

Traver et al., "A Neural Network-Based Virtual NOx Sensor for Diesel Engines," 7 pages, prior to Jan. 29, 2016.

Tschanz et al., "Cascaded Multivariable Control of the Combustion in Diesel Engines," The International Federation of Automatic Control (IFAC), 2012 Workshop on Engine and Powertrain Control, Simulation and Modeling, pp. 25-32, Oct. 23-25, 2012.

Tschanz et al., "Control of Diesel Engines Using NOx-Emission Feedback," International Journal of Engine Research, vol. 14, No. 1, pp. 45-56, 2013.

Tschanz et al., "Feedback Control of Particulate Matter and Nitrogen Oxide Emissions in Diesel Engines," Control Engineering Practice, vol. 21, pp. 1809-1820, 2013.

Turner, "Automotive Sensors, Sensor Technology Series," Momentum Press, Unable to Obtain the Entire Book, the Front and Back Covers and Table of Contents are Provided, 2009.

Van Basshuysen et al., "Lexikon Motorentechnik," (Dictionary of Automotive Technology) published by Vieweg Verlag, Wiesbaden 039936, p. 518, 2004. (English Translation).

Van Den Boom et al., "MPC for Max-Plus-Linear Systems: Closed-Loop Behavior and Tuning," Proceedings of the 2001 American Control Conference, Arlington, Va, pp. 325-330, Jun. 2001.

Van Helden et al., "Optimization of Urea SCR deNOx Systems for HD Diesel Engines," SAE International 2004-01-0154, 13 pages, 2004.

\* cited by examiner

INFERENTIAL SENSOR

This application is a continuation-in-part of International Application No. PCT/US2016/064036, filed Nov. 29, 2016. International Application No. PCT/US2016/064036, filed Nov. 29, 2016, is hereby incorporated by reference.

BACKGROUND

The present disclosure pertains to sensors, engines, and particularly to components related to emissions reduction of the engines.

SUMMARY

The disclosure reveals a system and an approach for determining various flows in an internal combustion engine, such as an amount of recirculation exhaust gas flow through a controlled valve, a fresh air mass flow to an intake of an engine, and a pressure at an inlet of a turbine which may also be the pressure at the inlet of a high pressure exhaust gas recirculation (EGR). The disclosure may reveal a method of how a pressure estimate may be useful for determining mass flow rates and/or intervals containing the determined mass flow rates.

DESCRIPTION

Figure 1:
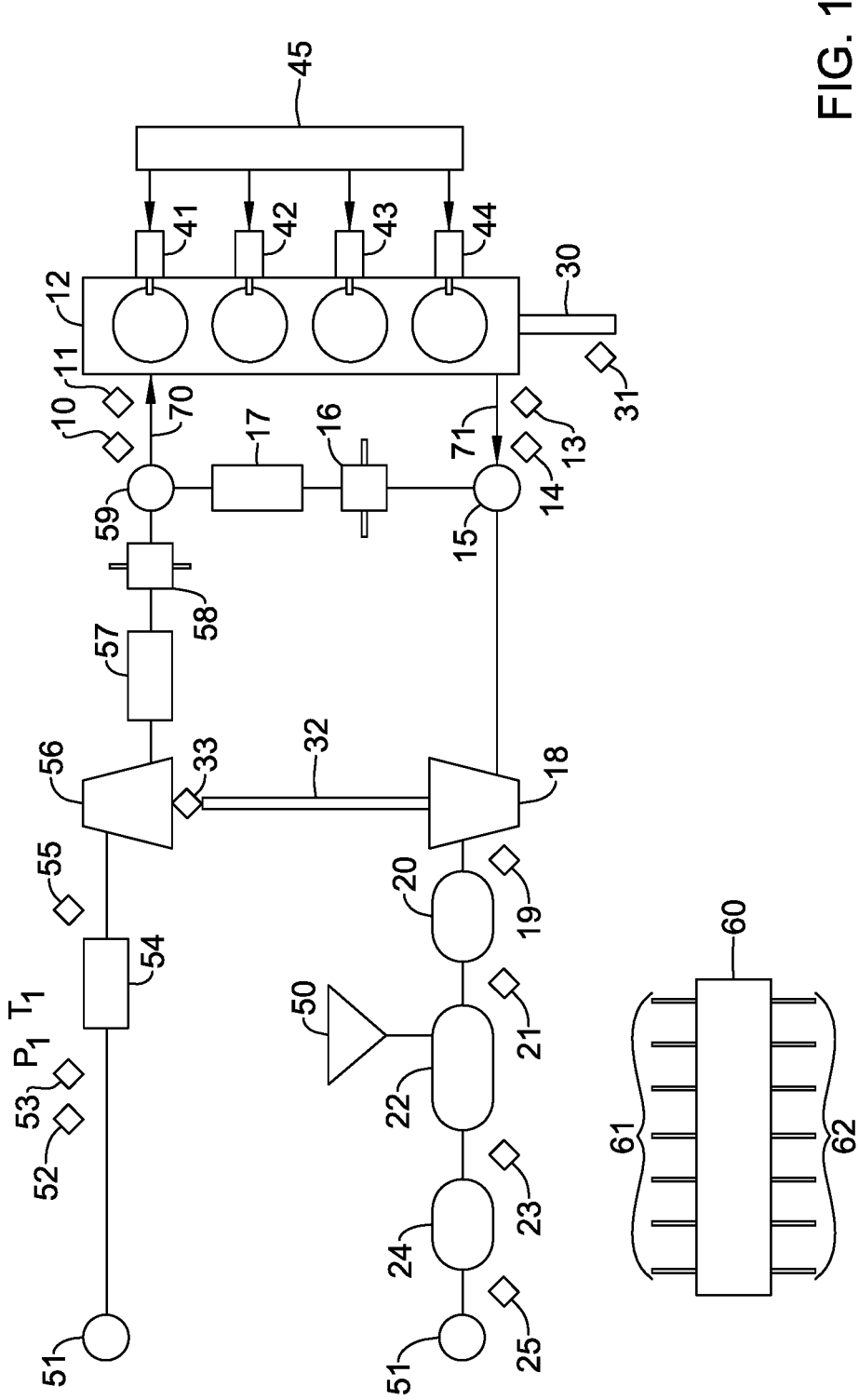
FIG. 1 is a diagram of a turbocharged diesel engine.

The present system and approach may incorporate one or more processors, computers, controllers, user interfaces, wireless and/or wire connections, and/or the like, in an implementation described and/or shown herein.

This description may provide one or more illustrative and specific examples or ways of implementing the present system and approach. There may be numerous other examples or ways of implementing the system and approach.

Aspects of the system or approach may be described in terms of symbols in the drawing. Symbols may have virtually any shape (e.g., a block) and may designate hardware, objects, components, activities, states, steps, procedures, and other items.

The mass flows in the turbocharged combustion engine, particularly the fresh air mass flow and the exhaust gas recirculation (EGR) mass flow, are important control parameters which need to be carefully controlled.

The fresh air mass flow may determine the oxygen availability for the fuel combustion. It may be noted that oxygen unavailability may lead to incomplete combustion and generation of soot particles which may either be observed as tailpipe smoke or which may clog the particulate filter. In combustion engines, both gasoline and diesel, the fresh air flow usually needs to be controlled to a desired ratio to the fuel mass flow.

The EGR mass flow may determine the portion of inert three atomic gases $H_2O$ and $CO_2$ in the gas charged to cylinders. An inert content may dissolve the oxygen and increase the thermal capacity of the charged gas. The increased thermal capacity and lowered oxygen availability of the charged gas may both lead to lower peak temperatures in a cylinder which reduces formation of nitrogen oxides NO and $NO_2$ (i.e., $NO_R$). The mass of these harmful oxides produced by engines may be regulated by emission limits.

Although the mass flows are important control parameters, they may not always be easily measured with a sufficient degree of accuracy, robustness, and reliability. Also a cost of such physical sensors may be considered high. The air mass flow sensors based on principles such as hot-film sensors (HFS), or EGR mass flow sensors based on a Venturi tube principle, can be associated with significant costs, calibration efforts, and reliability issues. It may be therefore practical to calculate the mass flows from other physical quantities which can be measured easier, especially if sensors for those physical quantities are already present in the system because of other control or monitoring functions. It may be noted that the physical flow sensors can either be replaced by the calculated values or the calculated values may be used to improve the physical sensor signal, or may be used to diagnose failures of those physical flow sensors.

The quantities which can be measured accurately and with significantly better reliability than mass flows may be the intake side pressures and temperatures, which are temperatures and pressures between the air intake up to the cylinder. The turbo-speed, and oxygen content, namely, oxygen mole fraction in the exhaust gas may also be measured reliably. It may be noted that measuring pressures and temperatures on the exhaust side may be significantly more difficult due to harsh conditions there that can include high temperatures, pressure pulsations, and combustion products such as water considering that water may freeze in winter, aggressive Sulphur compounds, and deposits of soot and oil residues.

A virtual mass flow sensor may calculate the fresh air mass flow, the EGR mass flow, or both, based on those other physical sensors which may be available easier. These calculations may be based on models of the engine components and equations, which describe how the components are coupled and how they interact.

FIG. 1 is a diagram of a turbocharged diesel engine. A system of the gas flows in the turbocharged diesel engine with a high pressure EGR valve is shown in the diagram. The diagram shows layout of an internal combustion engine 12 and its peripheral components related to air and fuel supply. Engine 12 may have an intake manifold 70 and an exhaust duct or manifold 71. Intake pressure ($p_2$) and temperature ($T_2$) may be detected with a pressure sensor 10 and a temperature sensor 11, respectively. Exhaust pressure ($p_3$) and temperature ($T_3$) may be detected with a pressure sensor 13 and a temperature sensor 14, respectively. However, most production engines will not necessarily be equipped with sensors 13 and 14 due to a difficulty with sensors placed on the exhaust side.

In operation, air may come in from an ambient environment 51 at an input pressure ($p_1$) and temperature ($T_1$) as indicated by pressure sensor 52 and temperature sensor 53, respectively, positioned before the air filter 54. The air may be compressed by a compressor 56 and flow to a mixing point or plenum 59. Since air becomes hotter when compressed, an engine charge air cooler (CAC) 57 may be used to reduce compressed air temperature. A throttle 58 may be placed downstream of compressor 56 in order to control the pressure in intake manifold 70.

Some exhaust gas may be fed from exhaust manifold 71 through a splitter 15 and through an EGR valve 16 and out of a valve through a cooler 17 to the mixing point or plenum 59 where charged air from the compressor 56 and exhaust gas from EGR valve 16 meet. EGR valve 16 may control an amount of EGR gas to plenum 59. Exhaust gas at an input of EGR valve 16 may have a pressure $p_3$ and a temperature $T_3$. Exhaust gas that is not directed toward EGR valve 16 may go to drive a turbine 18 which turns a shaft 32 at N rotations per unit of time or a rate of angular movement omega (ω) as indicated by a sensor 33. Shaft 32 may drive compressor 56 that outputs the compressed air.

The exhaust gas can pass through a number of aftertreatment devices removing harmful compounds. Firstly, the gas may be passing the diesel particulate filter (DPF) 20 to trap soot particles which may be later burned using just the exhaust heat (passive regeneration) or using an extra diesel fuel injector located at the filter inlet (active regeneration). Some diesel engines may also use a diesel oxidation catalyst (DOC, not shown). Then the gas may be treated in a selective catalyst reduction (SCR) device 22 where most of the nitrogen oxides may be converted into harmless diatomic nitrogen using urea injected by the dosing system 50. In order to control the amount of urea used, SCR device 22 may be equipped with inlet and outlet NOx sensors 21 and 23 which may also provide additional information of the oxygen concentration in the exhaust gas. SCR device 22 may use ammonia created from the urea as a reducing agent to reduce the nitrogen oxides. The excess ammonia which may pass unreacted from SCR 22 as a result of urea overdosing may be removed in the ammonia slip catalyst (AMOX) 24.

Engine 12 cylinders may also be a recipient of fuel via a line or tube 45 to fuel injectors 41, 42, 43 and 44. The fuel from injectors 41, 42, 43 and 44 may mix with the air and EGR gas to the cylinders of engine 12 for combustion to move the pistons and turn the crankshaft for a mechanical rotational output at a shaft 30. Engine speed may be measured by a sensor 31 at shaft 30. Other approaches may be used for measuring engine speed. A lambda or oxygen sensor 19 may be situated in an exhaust duct where an exhaust stream may flow such as, for example, after turbine 18, after DPF 20 as sensor 21, after SCR 22 as sensor 23, after AMOX 24 as sensor 25, or there may be several lambda sensors at several locations, simultaneously. The lambda sensor may be combined with a NOx sensor.

Some acronyms that may be used relative to engine aftertreatment technology may incorporate SCR (selective catalytic reduction), SCRF (SCR on filter), DPF (diesel particulate filter), DOC (diesel oxidation catalyst), LNT (lean NOx trap), and PNA (passive NOx adsorber).

The exhaust stream may mean turbine-out, DOC-out, DPF-out, SCR-in, SCR-out, and even tailpipe-out. Though the oxygen content does not necessarily change significantly in the exhaust stream, it may be affected by some of the oxidations in the aftertreatment devices. Exhaust configurations may consist of, for example, turbine-DOC–DPF–SCR and turbine-PNA/LNT/DOC+SCRF+SCR. The lambda or oxygen sensor may be situated virtually anywhere.

A processor 60 may receive inputs 61 from one or more sensors of sensors 52, 53, 33, 10, 11, 13, 14, 19, 21, 23, 25, via wire or wireless connections. An output 62 from processor 60 may be used for controlling EGR valve 16 or for controlling the throttle 58. Other components, such as coolers 57 and 17, variable geometry of turbine 18 or turbine waste gate, and injectors 41, 42, 43 and 44, may be controlled by outputs 62 from processor 60.

An engine configuration, such as the one in FIG. 1, together with mathematical models of the individual elements in the configuration, may define a set of equations from which the sought mass flow and/or pressure values can be solved. In particular, the mass conservation law in the engine configuration of FIG. 1 may define that the fresh air mass flow equals turbine mass flow minus fuel mass flow, and define that the EGR mass flow equals charged gas flow minus fresh air mass flow.

The equations may hold at any time up to small and negligible dynamic inaccuracies caused by mass accumulation in the intake and exhaust manifolds. It may be noted that from these equations the sought fresh air mass flow and sought EGR mass flow may be calculated indirectly by first calculating the charged gas mass flow $\dot{m}_{ch}$, the turbine mass flow $\dot{m}_t$ and the fuel mass flow $\dot{m}_f$, and calculating the fresh air flow $\dot{m}_a$ and EGR mass flow $\dot{m}_{EGR}$ in a second step. Below are explanations of how fuel, turbine, and charged gas mass flows can be calculated.

Values of a pressure $p_3$ and a temperature $T_3$ at the exhaust duct or manifold 71 may be parameters used to determine the mass flow rates through turbine and through the EGR valve. Estimating $p_3$ may be an important intermediate step in the process. The estimated mass flow rate through the turbine may be used for indirect estimation of the fresh air rate and EGR mass flow rate. The flows in the system may be related by linear equations representing the mass conservation in the engine:

$$\dot{m}_t = \dot{m}_a + \dot{m}_f$$

$$\dot{m}_{ch} = \dot{m}_a + \dot{m}_{EGR}$$

The fresh air and EGR mass flow rates may be estimated indirectly by calculating the turbine mass flow rate $\dot{m}_t$ and the EGR mass flow rates $\dot{m}_{EGR}$ using the turbine and EGR valve flow models and then solving the above equations. The fuel mass flow $\dot{m}_f$ may virtually always be calculated from the fuel injection quantity per cylinder stroke $q_f$ [mg/cyl/stroke], which may be known to the processor 60; also known is engine speed $N_e$ [rpm], and considering a four stroke engine with $N_{cyl}$ cylinders the fuel mass flow [kg/s] may be indicated by:

$$\dot{m}_f = N_{cyl} \frac{10^{-6}}{120} q_f N_e.$$

The charged gas mass flow $\dot{m}_{ch}$ [kg/s] may be expressed from engine rotational speed $N_e$ [rpm], the engine displacement volume $V_d$ [l], the intake manifold pressure $p_2$ [kPa] and temperature $T_2$ [K], the specific gas constant of the charged gas R [J/kg/K], and the volumetric efficiency parameter $\eta_{vol}$ [–] that may be a property of the engine and may depend on engine speed as well as other parameters such as the engine compression ratio, and the exhaust and intake pressures in view of:

$$\dot{m}_{ch} = \frac{1}{120} \eta_{vol}(N_e) V_d \frac{p_2}{T_2 R} N_e.$$

The turbine mass flow $\dot{m}_t$ [kg/s] may be calculated from the turbine inlet pressure $p_3$, turbine outlet pressure $p_4$, turbine inlet temperature $T_3$, and turbine speed $N_t$. Some turbines may have control parameters such as variable geometry or a waste gate. The basis for this calculation may be an experimental turbine map $M_t(N_t, p_{30}/p_4)$, which defines the turbine mass flow rate for fixed reference inlet pressure $p_{30}$ and temperature $T_{30}$. Using such turbine map, the turbine mass flow $\dot{m}_t$ may be calculated for any inlet pressure $p_3$ and temperature values $T_3$, $$\dot{m}_t = M_t(N_t\sqrt{T_3/T_{30}},\ p_3/p_4)p_3/p_{30}\sqrt{T_{30}/T_3}.$$

The above calculation of $\dot{m}_t$ may require the values $p_3$, $p_4$, $T_3$ which may not be sensed in some cases. However, other similar equations describing the model components can be added to define these values from available signals. The $T_3$ temperature may be estimated modeling the combustion, heat transfer and gas expansion processes in the cylinder. The post turbine pressure $p_4$ may be expressed considering a model of the flow restriction of the post turbine elements. It is virtually always possible to add equations to calculate the rough mass flows from signals known to processor 60. Engines with double stage turbochargers may have two turbines in a cascade. Maps of both turbines may be then used in the calculations.

The EGR mass flow $\dot{m}_{EGR}$ may be calculated from the following orifice equation, $$\dot{m}_{EGR} = A(u_{EGR})\frac{p_3}{\sqrt{T_3}}\Psi\left(\frac{p_3}{p_2}\right)\ [kg/s]$$

where $\Psi$ is a flow function that can be calibrated for a specific valve used, $p_3, T_3$ is pressure and temperature before the EGR valve in the exhaust duct, $p_2$ is pressure after the EGR valve in the intake manifold, and $u_{EGR}$ is a valve position opening angle or valve opening area.

In some cases, the above calculation of $\dot{m}_t$ may require the values $p_3$, $p_4$, $T_3$ which may not be directly sensed. Modern turbocharged engines may be equipped with a $p_2$ sensor. In some cases, pressure $p_3$ may be calculated. Determining pressure $p_3$ is not necessarily sufficient. The $p_4$, $T_3$ need to be determined as well. However, it may be noted that $T_3$ can be determined from the energy balance and engine efficiency (e.g., based on a combustion model), in a cylinder gas expansion model, and a cylinder wall heat loss model. The pressure $p_4$ may be determined from the models of the post turbine element. However, the turbine flow value will normally be most sensitive to errors in $p_3$. As a result, it may be desirable to determine pressure $p_3$.

An approach for determining pressure $p_3$ may be based on the differential equation of the turbo speed which is the mechanical power balance:

$$\frac{d\omega(t)}{dt} = \frac{P_t(t) - P_c(t)}{J\omega(t)}$$

Here $P_t(t)$ [W] is the mechanical power of the turbine, $P_c(t)$ [W] is the mechanical power of the compressor, and $\omega(t)$ [rad/s] is the angular velocity of the turbocharger with the assumed momentum of inertia J [kg·m$^2$].

The mechanical powers of both the turbine and the compressor may depend on pressures, flows, and temperatures around these components. These parameters may be approximated by a reversible isentropic compression formula. The formula may define the power required to compress a mass flow rate $\dot{m}$ [kg/s] from pressure $p_1$ and temperature $T_1$ to pressure $p_2$ is:

$$P = c_p \dot{m} T_1\left[\left(\frac{p_2}{p_1}\right)^{\frac{1-\gamma}{\gamma}} - 1\right]$$

Here $c_p$ [J/kg/K] is the gas specific heat capacity and $\gamma$ is dimensionless the gas specific heat ratio also known as Poisson constant. Because of the reversibility of the isentropic process, the same power, in theory, may again be recovered when expanding the same mass flow rate from $p_2$ back to $p_1$. Because the real process is not reversible, however, some power may be lost (e.g., more power may be needed and less power is recovered).

The loss may be formally represented by considering compressor efficiency parameter $\eta_c$ and turbine efficiency parameter $\eta_t$. Both correction factors may be between zero and one and the normal values range between 0.2 and 0.8 depending on the turbocharger operating point (turbine speed, pressure ratios, and mass flows rates). These efficiencies (e.g., correction factors) may be determined experimentally by running the turbocharger on a gas stand in a number of points. The powers of compressor and turbine may be expressed:

$$P_c(t) = \frac{1}{\eta_c}c_{p,a}\dot{m}_a T_a\left[\left(\frac{p_0}{p_1}\right)^{\frac{1-\gamma_a}{\gamma_a}} - 1\right]$$

$$P_t(t) = \eta_t c_{p,e}(\dot{m}_a + \dot{m}_f)T_3\left[\left(\frac{p_3}{p_4}\right)^{\frac{1-\gamma_e}{\gamma_e}} - 1\right]$$

Here, $p_0$ is an ambient pressure. Note that neither the specific heats $c_{p,a}, c_{p,e}$ nor Poisson constants $\gamma_a, \gamma_e$ for the compressor power $P_c$ and turbine power $P_t$ are the same values because the gas compositions are different. The gas composition for the compressor may be fresh air for the compressor and gas composition for the turbine may be exhaust gas (e.g., combustion products). Considering the compressor outlet pressure $p_1$ may be sensed (e.g., the engine does not have a throttle), or can be calculated from the sensed boost pressure $p_2$ subtracting the pressure drop over a throttle, the above equations can be used to solve for $p_3$ simultaneously with the flows.

When determining the pressure $p_3$, the temperature $T_3$ may be calculated before $p_3$, so it can be prepared before $p_3$ is solved. Further, although the unknown mass flow $\dot{m}_a$ appears in the above mechanical power balance equation, one can note that both compressor and turbine powers are multiplied by $\dot{m}_a$ and $\dot{m}_a + \dot{m}_f$ respectively. These values may be similar. It may be noted that $\dot{m}_f$ is at least 14.7 or 14.5 times smaller than $\dot{m}_a$ because it is the stoichiometric mass ratio of the gasoline and diesel fuels respectively. The unknown flow gets almost cancelled. Therefore the simultaneous solution of $\dot{m}_a$ and $p_3$ may be obtained by a rapidly converging iterative method. Although a simultaneous estimation of the throttle pressure drop and $p_4$ may make the solution more complicated, the principles may remain the same.

The above approach may be described as calculating $p_3$ which generates sufficient power to achieve the sensed boost pressure considering the turbine inlet temperature $T_3$, turbine and compressor efficiencies, turbocharger rotational speed $\omega(t)$, and turbine acceleration $d\omega(t)/dt$. For this reason, the above calculations may be used conveniently in connection with a physical turbo speed sensor installed on the engine. It may be noted that the turbo speed sensors may be very accurate and the signal allows for direct calculation of the acceleration using, for example, a filtered derivative (e.g., a time derivative) of the signal. Using such an estimate of the turbocharger acceleration, the $p_3$ may be correctly calculated even during significantly transient operation of the turbocharger.

When multiplying the mechanical power balance equation with $\eta_t$, it may become apparent that steady-state $p_3$ may depend almost exclusively on the product $\eta_t \eta_c$, not on the individual efficiencies independently. In fact, there is a marginal dependency on $\eta_c$ through $T_3$ because compressor efficiency slightly affects temperatures. However this may be neglected with very little impact. The main uncertain parameter in the equation may, thus, be the product $\eta_{tc} = \eta_t \eta_c$. The product represents the mechanical efficiency of the turbocharger as a whole, without distinguishing both components.

The approach may account for the uncertainty of $\eta_{tc}$. Both of the compressor and the turbine may have high efficiencies at an area of operating points, known as Efficiency Island. The efficiency may rapidly fall to zero on a border of the Efficiency Island. The estimated efficiency of the turbocharger is easier when both of the compressor and the turbine are in the Efficiency Islands, where the efficiency may be flat and almost constant. This is a general property of a smooth functions close to extreme points. On the border, off the peak efficiency, (e.g., the estimation of the actual turbocharger efficiency) may be problematic because the efficiency may be sensitive to actual turbo speed, output/input pressure ratios, or the mass flow rates. The $p_3$ estimate can thus be represented as an interval in which the actual $p_3$ may be contained, and the width of the interval may be based on the interval containing the true efficiency. This interval may be based on the turbine and the compressor efficiency maps and may account for various uncertainties and aging effects: the efficiency of a new turbocharger may be generally higher than the actual turbocharger in the vehicle.

Figure 2:
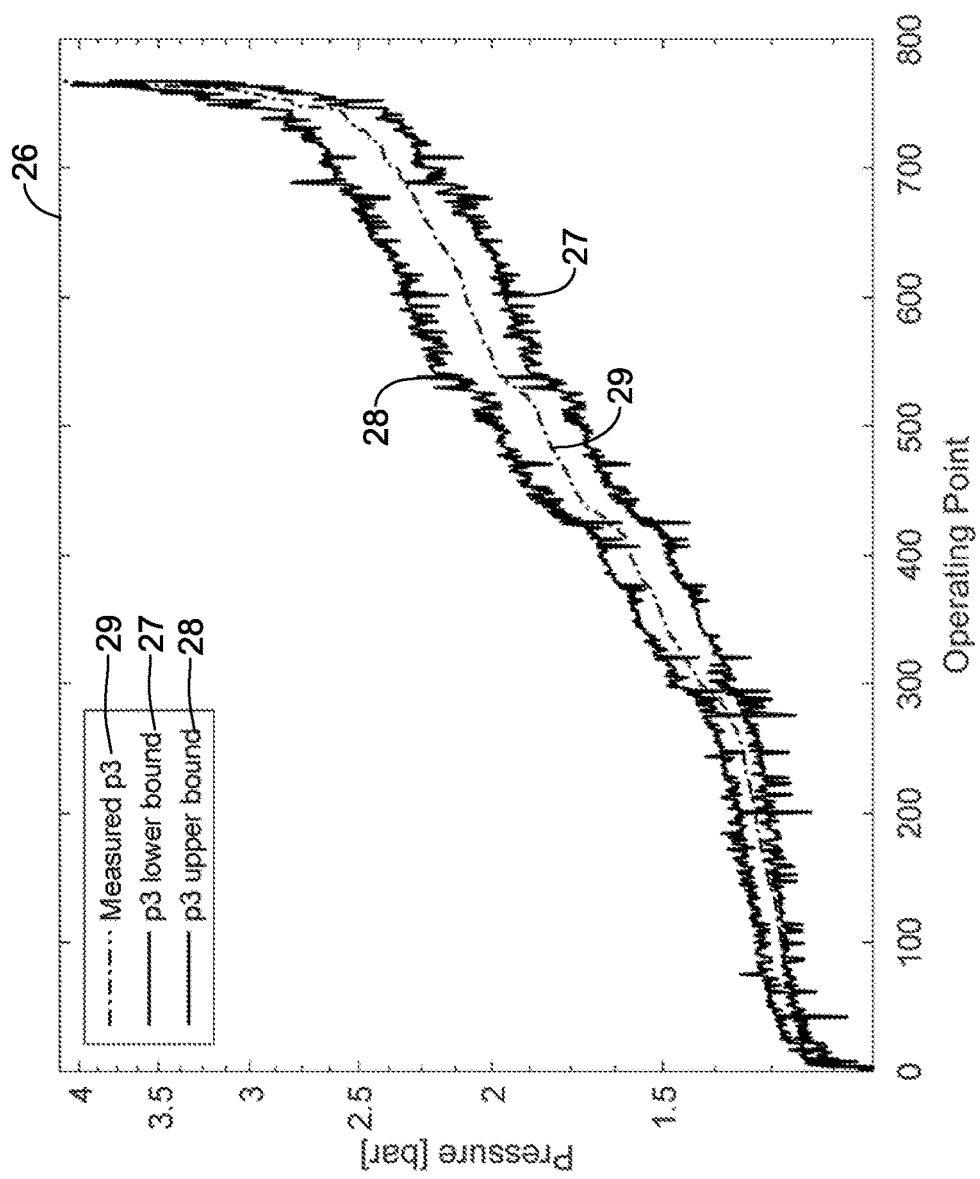
FIG. 2 is a schematic chart depicting an uncertainty interval containing a pressure based on an interval for efficiency compared with a pressure sensor installed on an engine for testing.

FIG. 2 is a schematic chart 26 depicting an uncertainty interval containing $p_3$ based on an interval for the efficiency compared with $p_3$ sensor installed on an engine for testing, where steady state data was sorted according to $p_3$. That is, FIG. 2 compares an estimated $p_3$ 29 with a $p_3$ interval represented by an estimated upper 28 and an estimated lower bound 27 derived from efficiency bounds. The lower $p_3$ bound 27 may provide the maximum turbocharger efficiency and the upper $p_3$ bound 28 may provide minimum turbocharger efficiency. Because the turbocharger efficiency cannot be higher than 1.0, the lower $p_3$ bound 27 may be reliable. It is possible to trust with a high degree of confidence that the true $p_3$ cannot be lower than the lower bound 27. The confidence in the upper bound 28 may be lower than the confidence in the lower bound 27 because the natural lower bound 27 on the turbocharger efficiency $\eta_{tc} > 0$ may lead to a useless bound on the pressure $p_3$, such as $p_3 < \infty$.

In some cases, it may be more difficult to find a realistic lower bound 27 for the efficiency than the upper bound 28. For example, the efficiency may not be higher than the peak efficiency of a new turbocharger of a given type.

Using the lower bound 27 on $p_3$, a lower bound on $\dot{m}_{EGR}$ may be derived using the valve flow model. At the same time, the lower bound on $\dot{m}_t$ can be derived using the turbine flow model. When combining this information together with the mass conservations equations, one gets both upper and lower bounds both based on the upper limit on the turbocharger efficiency:

$$\dot{m}_{EGR} > \dot{m}_{EGR,Low}$$

$$\dot{m}^{EGR} < \dot{m}_{ch} - \dot{m}_{t,Low} + \dot{m}_f$$

In some cases, the approach may include using the EGR valve flow model and the turbine flow model, both lower and upper bounds on EGR mass flow rate may be derived from just an upper bound on the turbocharger efficiency, which may be reliably set or determined. It may be noted that the same may hold for upper and lower bounds on the fresh air flow rate which can also be derived from just an upper bound on the turbocharger efficiency:

$$\dot{m}_a < \dot{m}_{ch} - \dot{m}_{EGR,Low}$$

$$\dot{m}_a > \dot{m}_{t,Low} - \dot{m}_f$$

It may be noted that just a one sided constraint on turbocharger efficiency may lead to two sided constraints on the unknown flows.

Further, the approach may include calculating the fresh air mass flow and/or the EGR mass flow utilizing the calculated fuel mass flow and the charge mass flow in view of on the mass conservation in the engine. The fact that EGR mass flow is both an input and output to these calculations is not necessarily contradictory. The EGR valve mass flow value defined by the valve characteristics may be corrected and made more accurate in the process when the mutual correlations between the flows are used.

The calculation may result in "fast" but possible offset estimates based on the model. A fast estimate means that there is no noticeable delay in the flow estimates relative to the true flow value. At the same time, the flow estimates may often be offset because the turbine characteristics, volumetric efficiency and valve flow function or valve cross section, as well as other properties, are never known accurately, and they may be subject to random changes or drifts during the vehicle life.

One distinctive feature of the present system may be how a lambda sensor is used to remove the offset from "fast" mass flow estimates that are based on a turbine model, EGR valve model, and engine volumetric efficiency model, and possibly other models. A lambda sensor, virtually located anywhere in the exhaust gas stream, may be used to correct the flow estimates reducing the offset. The lambda sensors may sense the oxygen mole fraction $O_2$ (e.g., oxygen content of exhaust gas) which is related to the fresh air mass flow and fuel mass flow. An exact relationship depends on the fuel composition and specific air humidity $H_s$ (water mass fraction in the air). As an example, the following relationship may be derived for fuel composition $C_{12}H_{23}$, $$\dot{m}_a = \frac{\dot{m}_f(3.065 + 0.992 O_2)}{0.21(1 - H_s) - O_2(1 + 0.602 H_s)}.$$

The above equation may define a way in how the fresh air mass flow $\dot{m}_a$ can be calculated from the lambda sensor; or from exhaust gas $O_2$ mole fraction, which was calculated from a lambda sensor output. However, it may be noted that such calculation may lead to a poor air flow estimate in numerous situations for the following reasons: 1) The lambda sensor output may be unavailable until it reaches sufficient temperature; 2) The denominator of the above formula is small and approaching zero for oxygen mole fractions close to 0.21 (that of dry fresh air), and the result of division may then have a very large relative error due to usually not accurately known, or completely unknown, air humidity and due to small but nonzero lambda sensor error; 3) The lambda sensor placed between or after the aftertreatment devices may further increase the error because being affected by oxidation reactions in the devices such as soot oxidation in the DPF; and 4) The lambda sensor can have significant delay up to 3 seconds and the $\dot{m}_a$ calculations may thus not be necessarily accurate during non-steady state operation of the engine. For these reasons, the $\dot{m}_a$ usually cannot be calculated from lambda directly at least when any of the above items (1-4) may play a role or when the lambda sensor is a low grade slow sensor.

Figure 3:
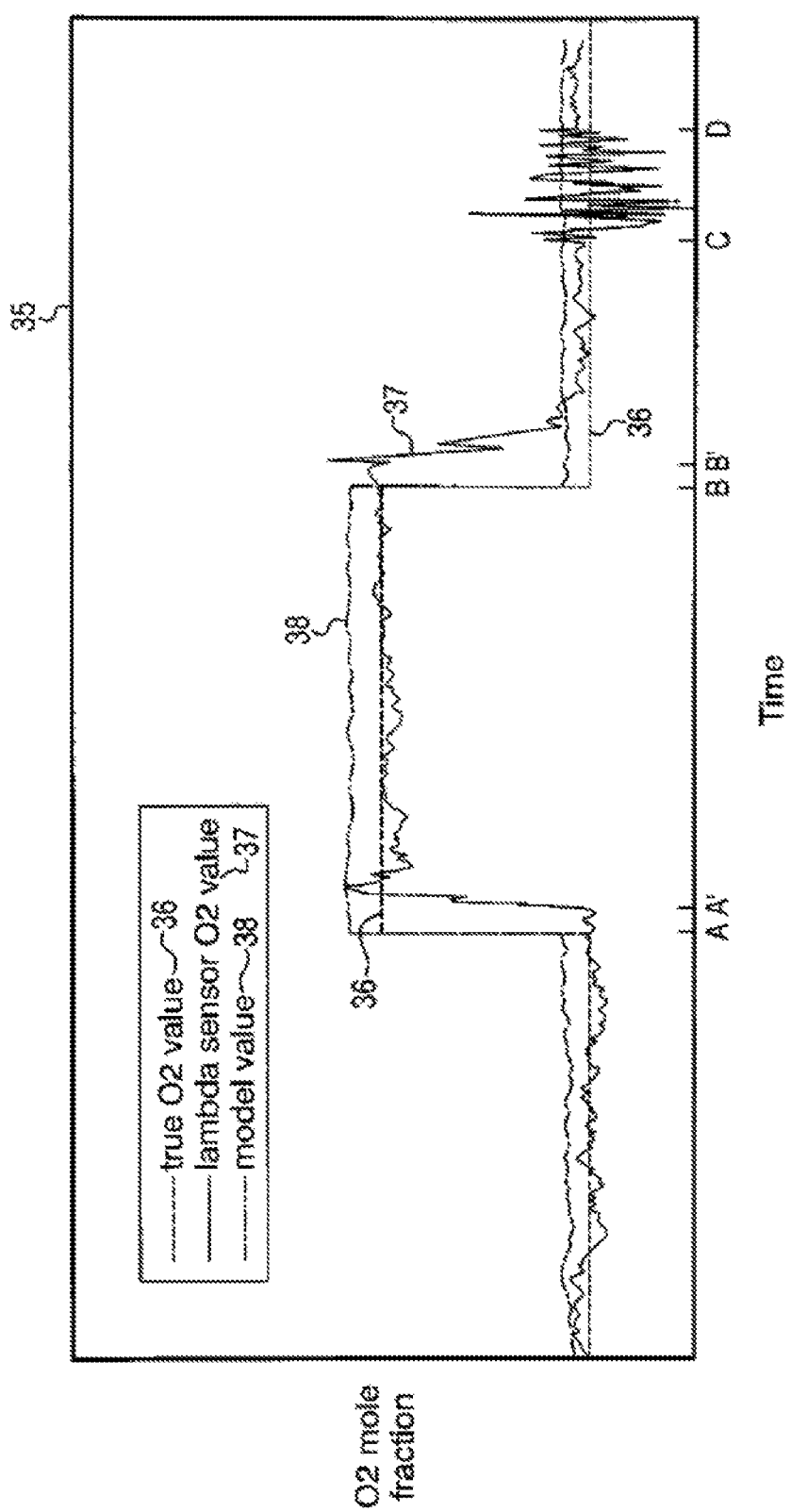
FIG. 3 is a diagram of a lambda sensor behavior graph.

FIG. 3 is a diagram of a lambda sensor behavior graph 35. A possible behavior of the $O_2$ mole fraction derived from lambda sensor signal 37 compared to the theoretical true $O_2$ value 36 and also value 38 calculated from the model equations is in graph 35. It may be noted that when the true $O_2$ value 36 changes at point A or B, the model may be able to predict the change without noticeable delay. However, the model predicted value 38 may be slightly offset for reasons explained before. The $O_2$ value 37 derived from the lambda signal will usually not be offset, or at least the offset will be smaller. However, it may take the lambda sensor (value 37) some time, A-A' or B-B', to reach the true $O_2$ value 36. Also, lambda sensor signal 37 may be noisy and difficult to interpret during transient periods between A-A' and B-B'. Moreover, lambda signal 37 may be affected by other processes, e.g., soot oxidations, and signal 37 may be sometimes temporarily inaccurate like between C and D.

A particular feature of the disclosure is an approach of calculating the theoretical "fast" lambda value 38 from the fuel mass flow, EGR mass flow and turbine mass flow estimates, which are not delayed but may be possibly offset. A lambda value 37 (having a dynamic delay) may be considered in a correction of flow estimates. The correction may slowly adjust the EGR valve and turbine model parameters to match the sensed lambda during more or less steady operation of the engine. The correction may be stronger or correction process may be faster when the lambda sensor operates in the favorable conditions and the lambda signal is steady. The correction may be almost none when the lambda sensor possibly operates in unfavorable conditions or during a transient. The correction may be based on calculated sensitivities of the lambda with respect to the adjusted parameters. This sensitivity calculation may involve lambda sensor model, including a dynamic model of the sensor delay, such as lambda sensor time constant and dead time. The correction process may be disengaged during periods of time the lambda not available, e.g., because the lambda sensor has not yet reached the working temperature after a cold start. It may be noted that the disclosed approach may still be providing valid flow estimates although the offset may not be fully corrected during these periods. Also considered in the correction may be a relationship between an $O_2$ mole fraction (i.e., a quantity sensed by the lambda sensor) and the air and fuel flows, and how this relationship may be affected by possibly uncertain air humidity.

Various approaches may be noted in the following text. An estimation approach may incorporate calculating fast but possibly offset EGR and air flow estimates using an intake manifold pressure sensor, and temperature sensors if available, turbocharger-speed sensor if available, as well as other available sensors, and finally correcting the offset of these estimates using a lambda sensor signal.

By fast but possibly offset estimates may mean that the flow estimates do not necessarily have any noticeable delay with respect to the true flows but they can be offset systematically because of parameter variations during a vehicle lifetime such as, for example, slow changes in the valve characteristics caused by fouling or soot deposits, or degradation of the turbocharger efficiency. By using the lambda signal, the offset may be removed.

An estimation approach may incorporate calculating fast but possibly an offset EGR and air flows combining EGR valve and turbine(s) plus post turbine elements (e.g., aftertreatment) mass flow models based on sensed or estimated inlet conditions $p_3$ and $T_3$, and making use of a turbo-speed sensor 33 if such turbo-speed sensor is available, which may parameterize the turbine mass flow model. For engines with two or more turbines, the approach may be generalized by treating the cascade of turbines almost as the single turbine.

An estimation approach may incorporate calculating fast but possibly offset EGR and air flows by combining the EGR valve and turbine(s) plus post turbine elements (e.g., aftertreatment) mass flow models where the relative contributions of the EGR valve and turbine(s) plus post turbine elements flow models are changed dynamically reflecting a variability of the accuracies of the flow models which may depend on current pressure ratios. An approach may incorporate estimating $T_3$ using a simplified combustion process model and estimating $p_3$ using a turbocharger model.

An estimation approach may combine a dynamically correct (fast) but possibly offset EGR and air flow estimates with a lambda signal to remove the steady-state offset during periods of time lambda signal is healthy and making use of low frequency component of the lambda signal instead of converting the lambda signal to the air mass flow directly.

An approach may incorporate combining the fast but possibly offset flow estimates with a slow lambda signal using a lambda sensor dynamic model (e.g., a transfer function modelling the lambda sensor dynamics, sensor time constant or interval for an unknown or randomly varying sensor time constant, and sensor dead time, or interval for unknown or randomly varying sensor dead time, or similar statistical, probabilistic, or interval sensor models).

An approach may incorporate adjusting the turbine efficiency, EGR valve flow functions, or other model properties to match the $O_2$ mole fraction sensed by lambda sensor in a steady-state.

A lambda sensor in the noted approaches of the present system may have performance specifications of delay ranging between 1 and 3 seconds depending on the flow velocity and gas parameters, and accuracy often worse than 2 percent. A greater part of the sensor inaccuracy may not necessarily be a property of the lambda sensor but due to additional processes in the system in the aftertreatment. The lambda sensors located in the aftertreatment may be partly affected by chemical reactions in the aftertreatment, some of which may change the oxygen mole fraction to certain degree. This may further decrease the accuracy of the air flow calculation from these sensors. Such a signal may be regarded as poor compared to many typical lambda sensors which may have performance accuracy specifications 2 percent or better. Although such lambda signals may be inappropriate for direct conversion to the air mass flow signal, they may be used to adjust the uncertain or drifting model parameters. Such lambdas located in the in the aftertreatment may be a quite inexpensive solution for the purpose of inferential sensing because they may already be installed for the purposes of aftertreatment control, e.g., urea dosing control, and they may be reused by the inferential sensor.

A distinctive feature of the proposed inferential sensing approach may use the lambda signal for a purpose of model parameters adaptations, e.g., to detect random changes in the system parameters over the vehicle lifetime. At the same time, lambda is not necessarily used to calculate the air flow directly. Therefore, the $O_2$ sensing sensors which would not be suitable for such conversion due to large dynamic delay may still be used.

Lambda may be a part of the $NO_x$ sensor. By further noting that the lambda signal has a lag, one may distinguish the present system from other systems on this characteristic, which may use lambda, and may calculate the fresh air flow from lambda directly using known correlations between lambda, air flow, and fuel mass flow. The present system may challenge a use of laggy lambda signals. Laggy signals of an instrument or detector may lag in that they are slow in revealing or indicating a parameter, characteristic, property, or the like being detected, measured, indicated, and/or so forth. Time delays typically encountered when using the lambda in the $NO_x$ sensor may range from 1 to 3 seconds, and the delays may vary depending on the conditions in the exhaust system and may be thus better characterized as intervals of delays or probability of delay values. Furthermore, a lambda sensor signal from an aftertreatment may not necessarily only be delayed but it may simply be almost random during a heavily transient operation. An advantage of the subject lambda is low cost and an easy adaption of the lambda to the inferential determination of EGR mass flow in the present system and approach.

To recap, an inferential exhaust manifold pressure detection device may incorporate an exhaust gas recirculation (EGR) valve having a first input, an output and a second input, an exhaust manifold of an engine having an output connected to the first input of the EGR valve and to an input of a turbine, and having an input connected to exhaust ports of cylinders of the engine, an intake manifold of the engine having an input connected to the output of the EGR valve and to an output of a compressor, and an output connected to intake ports of the cylinders, a pressure sensor situated in the intake manifold, and a processor having an input connected to the pressure sensor and an output. The processor may calculate an inlet pressure of the EGR valve based on a pressure from the pressure sensor. Further, the processor determines a control signal for the EGR valve based on the calculated inlet pressure of the EGR and outputs the control signal to the EGR valve.

The processor may derive the calculated EGR valve inlet pressure using a turbine power versus compressor power balance in view of an efficiency of the turbine and an efficiency of the compressor.

The processor may determine the compressor power balance based on a turbocharger angular velocity signal from a physical turbo speed sensor. Further, the processor may derive a power of a turbocharger acceleration from a time derivative of the turbocharger angular velocity signal.

The processor may calculate the inlet pressure of the EGR valve as an interval of possible values based on intervals of turbocharger efficiency.

The intervals of turbocharger efficiency may be a product of a compressor efficiency and a turbine efficiency and the processor may determine a maximum value of the product by finding a maximum value in the turbocharger map.

The processor may calculate a lower bound for the inlet pressure of the EGR valve based on a maximum possible turbocharger efficiency.

The processor may use the lower bound for the inlet pressure of the EGR valve to calculate an interval containing a fresh air mass flow rate and an interval containing an EGR mass flow rate.

The processor may detect an EGR valve blockage based on an upper bound on an EGR mass flow rate when determining that the EGR mass flow rate is not sufficient for a given valve opening angle.

The processor may detect an intake system air leakage based on a lower bound on a fresh mass flow rate when determining the fresh mass flow rate.

The processor may detect one or both of an EGR valve failure and an intake air leakage failure when a turbocharger efficiency is in an Efficiency Island.

The processor may be blocked from detecting an EGR valve failure and an intake air leakage failure when the turbocharger efficiency is outside of the Efficiency Island.

An inferential mechanism for determining pressure in an exhaust manifold may incorporate an exhaust manifold having a first input connected to an exhaust of an engine and having an output, an exhaust gas recirculation (EGR) valve having a first input connected to the output of the exhaust manifold and an output, an intake manifold of the engine having an input connected to the output of the EGR valve and an output, a pressure sensor situated in the intake manifold, a processor having an input connected to the pressure sensor and an output. The processor may calculate an inlet pressure of the EGR valve based on a pressure from the pressure sensor. Further, the processor may determine a control signal for the EGR valve based on the calculated inlet pressure of the EGR valve and outputs the control signal to the EGR valve.

The processor may derive the calculated EGR valve inlet pressure using a turbine power versus compressor power balance in view of an efficiency of a turbine connected to the output of the exhaust manifold and an efficiency of a compressor connected to the input of the intake manifold. The processor may determine a compressor power balance based on a turbocharger angular velocity signal from a physical turbo speed sensor. Further, the processor may derive a power of a turbocharger acceleration from a time derivative of the turbocharger angular velocity signal.

The processor may calculate the inlet pressure of the EGR valve as an interval of possible values based on intervals of turbocharger efficiency.

The processor may calculate a lower bound for the inlet pressure of the EGR valve based on a maximum possible turbocharger efficiency.

The processor may use the lower bound for the inlet pressure of the EGR valve to calculate an interval containing a fresh air mass flow rate and an interval containing an EGR mass flow rate.

The processor may detect an EGR valve blockage based on an upper bound on an EGR mass flow rate when determining that the EGR mass flow rate is not sufficient for a given valve opening angle.

The processor may detect an intake system air leakage based on a lower bound on a fresh mass flow rate when determining the fresh mass flow rate.

An approach for inferring a pressure at an exhaust manifold of an engine having a turbocharger may incorporate detecting a pressure in an intake manifold connected to an engine, calculating an inlet pressure of an exhaust manifold connected to the engine based on the detected pressure in the intake manifold and a turbine power versus compressor power balance, determining a control signal for an exhaust gas recirculation (EGR) valve based on the calculated inlet pressure in the exhaust manifold, and outputting the control signal for the EGR valve to the EGR valve.

The approach may include the inlet pressure of the exhaust manifold being calculated as an interval of possible values based on intervals of turbocharger efficiency.

Any publication or patent document noted herein is hereby incorporated by reference to the same extent as if each publication or patent document was specifically and individually indicated to be incorporated by reference.

In the present specification, some of the matter may be of a hypothetical or prophetic nature although stated in another manner or tense.

Although the present system and/or approach has been described with respect to at least one illustrative example, many variations and modifications will become apparent to those skilled in the art upon reading the specification. It is therefore the intention that the appended claims be interpreted as broadly as possible in view of the related art to include all such variations and modifications.

What is claimed is:

1. An inferential exhaust manifold pressure detection device comprising:
    an exhaust gas recirculation (EGR) valve having a first fluid input, a fluid output and a second fluid input;
    an exhaust manifold of an engine having a fluid output connected to the first fluid input of the EGR valve and to a fluid input of a turbine, and having a fluid input connected to exhaust ports of cylinders of the engine;
    an intake manifold of the engine having a fluid input connected to the fluid output of the EGR valve and to a fluid output of a compressor, and a fluid output connected to intake ports of the cylinders;
    a pressure sensor situated in the intake manifold; and
    a processor having an electrical signal input connected to the pressure sensor and an electrical signal output; and
    wherein:
        the processor calculates an inlet pressure of the EGR valve based on a pressure from the pressure sensor;
        the processor derives the calculated EGR valve inlet pressure using a turbine power versus compressor power balance in view of an efficiency of the turbine and an efficiency of the compressor; and
        the processor determines a control signal for the EGR valve based on the calculated inlet pressure of the EGR and outputs the control signal to the EGR valve.

2. The device of claim 1, wherein the processor:
    determines the compressor power balance based on a turbocharger angular velocity signal from a physical turbo speed sensor; and
    derives a power of a turbocharger acceleration from a time derivative of the turbocharger angular velocity signal.

3. The device of claim 1, wherein the processor calculates the inlet pressure of the EGR valve as an interval of possible values based on intervals of turbocharger efficiency.

4. The device of claim 3, wherein the intervals of turbocharger efficiency are a product of a compressor efficiency and a turbine efficiency and the processor determines a maximum value of the product by finding a maximum value in the turbocharger map.

5. The device of claim 1, wherein the processor calculates a lower bound for the inlet pressure of the EGR valve based on a maximum possible turbocharger efficiency.

6. The device of claim 5, wherein the processor uses the lower bound for the inlet pressure of the EGR valve to calculate an interval containing a fresh air mass flow rate and an interval containing an EGR mass flow rate.

7. The device of claim 1, wherein the processor detects an EGR valve blockage based on an upper bound for an EGR mass flow rate when determining that the EGR mass flow rate is not sufficient for a given valve opening angle.

8. The device of claim 1, wherein the processor detects an intake system air leakage based on a lower bound on a fresh mass flow rate when determining the fresh mass flow rate.

9. The device of claim 1, wherein the processor detects one or both of an EGR valve failure and an intake air leakage failure when a turbocharger efficiency is in an Efficiency Island.

10. The device of claim 9, wherein the processor is blocked from detecting an EGR valve failure and an intake air leakage failure when the turbocharger efficiency is outside of the Efficiency Island.

11. An inferential mechanism for determining pressure in an exhaust manifold an engine having a turbocharger comprising:
    an exhaust manifold having a first fluid input connected to an exhaust of an engine and having a fluid output;
    an exhaust gas recirculation (EGR) valve having a first fluid input connected to the fluid output of the exhaust manifold and having a fluid output;
    an intake manifold of the engine having a fluid input connected to the fluid output of the EGR valve and having a fluid output;
    a pressure sensor situated in the intake manifold; and
    a processor having an electrical signal input connected to the pressure sensor and having an electrical signal output; and
    wherein the processor:
        calculates a lower bound for an inlet pressure of the EGR valve based on a maximum possible turbocharger efficiency;
        uses the lower bound for the inlet pressure of the EGR valve to calculate an interval containing a fresh air mass flow rate;
        detects a fuel injection offset using the interval on a fresh air mass flow rate; and
        determines a control signal to adjust fuel injection in view of the fuel injection offset and outputs the control signal to a fuel injector.

12. The mechanism of claim 11, further comprising:
    a lambda sensor having an electrical signal output connected to the electrical signal input of the processor; and
    wherein the processor detects the fuel injection offset using the interval on a fresh air mass flow rate by comparing the interval on a fresh air mass flow rate with an interval on a fresh air mass flow rate derived from a lambda sensor.

13. The mechanism of claim 11, further comprising:
    a fresh air mass flow rate physical sensor having an electrical signal output connected to the electrical signal input of the processor; and
    wherein the processor detects a fresh air mass flow rate physical sensor offset by comparing the interval on a fresh air mass flow rate sensed with a fresh air mass flow rate physical sensor.

14. The mechanism of claim 11, wherein the processor:
    calculates an inlet pressure of the EGR valve based on a pressure from the pressure sensor; and
    determines a control signal for the EGR valve based on the calculated inlet pressure of the EGR and outputs the control signal to the EGR valve.

15. The mechanism of claim 14, wherein the processor:
    derives the calculated EGR valve inlet pressure using a turbine versus compressor power balance in view of an efficiency of a turbine connected to the output of the exhaust manifold and an efficiency of a compressor connected to the input of the intake manifold;

determines a compressor power balance based on a turbocharger angular velocity signal from a physical turbo speed sensor; and derives a power of a turbocharger acceleration from a time derivative of the turbocharger angular velocity signal.

16. The mechanism of claim 14, wherein the processor calculates the inlet pressure of the EGR valve as an interval of possible values based on intervals of turbocharger efficiency.

17. The mechanism of claim 14, wherein the processor detects an EGR valve blockage based on an upper bound on an EGR mass flow rate when determining that the EGR mass flow rate is not sufficient for a given valve opening angle.

18. A method for inferring a pressure at an exhaust manifold of an engine having a turbocharger, the method comprising:

detecting a pressure in an intake manifold connected to an engine;

calculating an inlet pressure of an exhaust manifold connected to the engine based on the detected pressure in the intake manifold and a turbine power versus compressor power balance;

determining a control signal for an exhaust gas recirculation (EGR) valve based on the calculated inlet pressure in the exhaust manifold;

outputting the control signal for the EGR valve to the EGR valve; and wherein the inlet pressure of the exhaust manifold is calculated as an interval of possible values based on intervals of turbocharger efficiency.

* * * * *